(12) United States Patent
Kuechler et al.

(10) Patent No.: US 7,678,953 B2
(45) Date of Patent: *Mar. 16, 2010

(54) OLEFIN OLIGOMERIZATION

(75) Inventors: Keith H. Kuechler, Friendswood, TX (US); Stephen Harold Brown, Bernardsville, NJ (US); An Amandine Verberckmoes, Serskamp (BE); Marc P. Puttemans, Schepdaal (BE); Steven E. Silverberg, Seabrook, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 911 days.

This patent is subject to a terminal disclaimer.

(21) Appl. No.: 11/342,000

(22) Filed: Jan. 27, 2006

(65) Prior Publication Data

US 2006/0199987 A1 Sep. 7, 2006

Related U.S. Application Data

(60) Provisional application No. 60/648,947, filed on Jan. 31, 2005, provisional application No. 60/648,938, filed on Jan. 31, 2005, provisional application No. 60/727,563, filed on Oct. 17, 2005.

(51) Int. Cl.
*C07C 2/02* (2006.01)

(52) U.S. Cl. ............... 585/502; 585/1; 585/14; 585/504; 585/517; 585/520; 585/533; 585/716; 585/722; 502/42; 502/44

(58) Field of Classification Search ............ 585/1, 585/14, 502, 504, 517, 520, 533, 716, 722; 502/42, 44

See application file for complete search history.

(56) References Cited

U.S. PATENT DOCUMENTS 3,926,782 A  12/1975  Plank et al.

(Continued)

FOREIGN PATENT DOCUMENTS

EP  0 882 692  12/1998

(Continued)

OTHER PUBLICATIONS

N. Amin, et al., "Dealuminated ZSM-5 Zeolite Catalyst for Ethylene Oligomerization to Liquid Fuels", Journal of Natural Gas Chemistry, vol. 11, pp. 79-86, 2002. (Abstract).

(Continued)

*Primary Examiner*—Glenn Caldarola
*Assistant Examiner*—Prem C. Singh
(74) *Attorney, Agent, or Firm*—Kevin M. Faulkner; David M. Weisberg

(57) ABSTRACT

A process for producing a hydrocarbon composition that comprises contacting a feed stream, that comprises at least one $C_3$ to $C_8$ olefin, and an olefinic recycle stream, that comprises a first olefinic recycle stream and no more than 10 wt % of $C_{10}$+ non-normal olefins, with a molecular sieve catalyst in a reaction zone under olefin oligomerization conditions producing an oligomerization effluent stream; separating the oligomerization effluent stream to produce a first olefinic stream, that has a weight ratio of $C_4$-/($C_5$-$C_8$) molecules from about 0.8 to about 1.2 times the weight ratio of $C_4$-/($C_5$-$C_8$) molecules found in the oligomerization effluent stream, and a first hydrocarbon product stream, that comprises at least 1 wt % and no more than 30 wt % of $C_9$ non-normal olefin; and splitting the first olefinic stream to produce the first olefinic recycle stream and a first purge stream.

48 Claims, 1 Drawing Sheet

U.S. PATENT DOCUMENTS

| | | | |
|---|---|---|---|
| 4,025,575 A | 5/1977 | Chang et al. |
| 4,211,640 A | 7/1980 | Garwood et al. |
| 4,263,141 A | 4/1981 | Möller et al. |
| 4,369,255 A | 1/1983 | Supp |
| 4,444,988 A | 4/1984 | Capsuto et al. |
| 4,456,781 A | 6/1984 | Marsh et al. |
| 4,471,147 A | 9/1984 | Owen et al. |
| 4,482,772 A | 11/1984 | Tabak |
| 4,497,968 A | 2/1985 | Wright et al. |
| 4,504,693 A | 3/1985 | Tabak et al. |
| 4,543,435 A | 9/1985 | Gould et al. |
| 4,544,792 A | 10/1985 | Smith et al. |
| 4,547,612 A | 10/1985 | Tabak |
| 4,547,616 A | 10/1985 | Avidan et al. |
| 4,560,536 A | 12/1985 | Tabak |
| 4,677,243 A | 6/1987 | Kaiser |
| 4,720,600 A | 1/1988 | Beech, Jr. et al. |
| 4,740,645 A | 4/1988 | Garwood et al. |
| 4,777,316 A | 10/1988 | Harandi et al. |
| 4,788,366 A | 11/1988 | Harandi et al. |
| 4,822,477 A | 4/1989 | Avidan et al. |
| 4,831,203 A | 5/1989 | Owen et al. |
| 4,831,204 A | 5/1989 | Kushnerick et al. |
| 4,834,949 A | 5/1989 | Owen et al. |
| 4,851,602 A | 7/1989 | Harandi et al. |
| 4,855,524 A | 8/1989 | Harandi et al. |
| 4,859,308 A | 8/1989 | Harandi et al. |
| 4,868,146 A | 9/1989 | Chu et al. |
| 4,873,385 A | 10/1989 | Avidan et al. |
| 4,873,389 A | 10/1989 | Avidan et al. |
| 4,877,921 A | 10/1989 | Harandi et al. |
| 4,879,428 A | 11/1989 | Harandi et al. |
| 4,899,014 A | 2/1990 | Avidan et al. |
| 4,919,896 A | 4/1990 | Harandi et al. |
| 4,935,568 A | 6/1990 | Harandi et al. |
| 4,939,314 A | 7/1990 | Harandi et al. |
| 4,942,021 A | 7/1990 | Garwood et al. |
| 4,966,680 A | 10/1990 | Avidan et al. |
| 5,019,357 A | 5/1991 | Harandi et al. |
| 5,034,565 A | 7/1991 | Harandi et al. |
| 5,043,499 A | 8/1991 | Harandi et al. |
| 5,043,517 A * | 8/1991 | Haddad et al. ............... 585/533 |
| 5,057,640 A | 10/1991 | Chang et al. |
| 5,059,744 A | 10/1991 | Harandi et al. |
| 5,063,187 A | 11/1991 | Burgfels et al. |
| 5,146,032 A | 9/1992 | Harandi |
| 5,177,279 A | 1/1993 | Harandi |
| 5,210,347 A | 5/1993 | Chen et al. |
| 5,234,875 A | 8/1993 | Han et al. |
| 6,169,218 B1 | 1/2001 | Hearn et al. |
| 6,548,721 B1 | 4/2003 | McCulloch et al. |
| 6,673,978 B2 | 1/2004 | Coute' et al. |
| 6,723,889 B2 | 4/2004 | Miller et al. |
| 7,253,330 B2 | 8/2007 | Dakka et al. |
| 2001/0001803 A1 | 5/2001 | Hubbard et al. |
| 2002/0020107 A1 | 2/2002 | Bailey et al. |
| 2003/0085153 A1 | 5/2003 | O'Rear |
| 2003/0116469 A1 | 6/2003 | Hemighaus et al. |
| 2004/0034261 A1 | 2/2004 | O'Reilly et al. |
| 2004/0068923 A1 | 4/2004 | O'Rear et al. |
| 2004/0148850 A1 | 8/2004 | O'Rear et al. |
| 2004/0149626 A1 | 8/2004 | O'Rear et al. |
| 2004/0152792 A1 | 8/2004 | O'Rear et al. |
| 2004/0152930 A1 | 8/2004 | O'Rear et al. |

FOREIGN PATENT DOCUMENTS

| | | |
|---|---|---|
| EP | 0 916 716 | 5/1999 |
| EP | 1 013 744 | 6/2000 |
| EP | 1 154 009 | 11/2001 |
| EP | 1 249 486 | 10/2002 |
| EP | 1 359 207 | 11/2003 |
| EP | 1 457 546 | 9/2004 |
| WO | WO 00/20534 | 4/2000 |
| WO | WO 00/20535 | 4/2000 |
| WO | WO 01/19762 | 3/2001 |
| WO | WO 01/49812 | 7/2001 |
| WO | WO 01/62875 | 8/2001 |
| WO | WO 02/04575 | 1/2002 |
| WO | WO 02/092731 | 11/2002 |
| WO | WO 03/104361 | 12/2003 |
| WO | WO 2004/16572 | 2/2004 |
| WO | WO 2004/18089 | 3/2004 |
| WO | WO 2004/033512 | 4/2004 |
| WO | WO 2005/003262 | 1/2005 |

OTHER PUBLICATIONS

S. Schwarz et al., "Effect of Silicon-to-Aluminium Ratio and Synthesis Time on High-Pressure Olefin Oligomerization over ZSM-5", Applied Catalysis, vol. 56, pp. 263-280, Dec. 15, 1989.

S. Inagaki, et al., "Influence of nano-particle agglomeration on the catalytic properties of MFI zeolite", Studies in Surface Science and Catalysis, vol. 135, pp. 566-572, 2001.

P. Yarlagadda, et al, "Oligomerization of Ethene and Propene over Composite Zeolite Catalysts", Applied Catalysis, vol. 62, pp. 125-139, Jun. 20, 1990.

M. Yamamura et al., "Synthesis of ZSM-5 zeolite with small crystal size and its catalytic performance for ethylene oligomerization", Zeolites, vol. 14, pp. 643-649, Nov.-Dec. 1994.

Weekman, V. Jr.; "A Model of Catalytic Cracking Conversion in Fixed, Moving, and Fluid-Bed Reactors," Applied Research & Development Division, vol. 7, No. 1, pp. 90-95, 1968.

Pivovarov, A. T. et al.; "Control Parameters for Catalytic Cracking," UDC No. 66.012.52: 542.97, pp. 317-320.

Lee J.S.; et al.; "Effects of Space Velocity on Methanol Synthesis from $CO_2/CO/H_2$ over $Cu/ZnO/Al_2O_3$ Catalyst," Korean J. Chem. Eng, vol. 17, pp. 332-337, 2000.

Fürcht, Á., et al.; "N-Octane Reforming: Conversion and Selectivity Dependence on Space Velocity," React. Kinet. Catal. Lett., vol. 72, No. 2, pp. 269-275, 2001.

Hengstebeck, R.J., "Polymerization and Alkylation," Petroleum Processing, Principles and Applications, pp. 208-218, 1959.

Lu Wen-Zhi, et al.; "Theoretical Analysis of Fluidized-Bed Reactor for Dimethyl Ether Synthesis from Syngas," International Journal of Chemical Reactor Engineering, vol. 1, pp. 1-10, 2003.

* cited by examiner

OLEFIN OLIGOMERIZATION

CROSS REFERENCE TO RELATED APPLICATIONS

This application claims the benefit of U.S. Provisional Application 60/648,947, filed Jan. 31, 2005; U.S. Provisional Application No. 60/648,938, filed Jan. 31, 2005; and U.S. Provisional Application No. 60/727,563, filed Oct. 17, 2005, all of which are fully incorporated herein by reference. The present application is related by subject matter to co-pending U.S. patent application Ser. No. 11/342,374, filed Jan. 27, 2006; U.S. patent application Ser. No. 11/342,385, filed Jan. 27, 2006; U.S. patent application Ser. No. 11/342,386, filed Jan. 27, 2006; and U.S. patent application Ser. No. 11/342,365, filed Jan. 27, 2006.

FIELD OF THE INVENTION

This invention relates to an olefin oligomerization process for producing hydrocarbon compositions useful as fuels, such as jet fuel and diesel fuel.

BACKGROUND OF THE INVENTION

Improved hydrocarbon compositions are needed to help meet the growing demand for middle distillate products, such as aviation turbine fuels, for example, JP-8 and diesel fuel. Diesel fuel generally provides a higher energy efficiency in compression ignition engines than automotive gasoline provides in spark combustion engines, and has a higher rate of demand growth than automotive gasoline, especially outside the U.S. Further, improved fuel compositions are needed to meet the stringent quality specifications for aviation fuel and the ever tightening quality specifications for diesel fuel as established by industry requirements and governmental regulations.

One known route for producing hydrocarbon compositions useful as fuels is the oligomerization of olefins over various molecular sieve catalysts. Exemplary patents relating to olefin oligomerization include U.S. Pat. Nos. 4,444,988; 4,497,968; 4,482,772; 4,720,600 and 4,879,428. In these disclosures, feedstock olefins are mixed with an olefinic recycle material and contacted with a zeolite, particularly in a series of fixed bed reactors. The oligomerized reaction product is then separated to provide a distillate stream, and typically a gasoline stream, and any number of olefinic recycle streams.

However, in these known oligomerization processes, the focus is on producing relatively heavy distillate products, and even lube base stocks. To enable the production of relatively heavy materials, the processes employ, either directly or indirectly, a relatively large amount of olefinic recycle containing significant quantities of $C_{10}+$ material. The relatively large recycle rate provides control over the exotherm of the oligomerization reaction in the preferred fixed bed, adiabatic reactor system, while the relatively heavy recycle composition enables the growth of heavier oligomers and thus higher molecular weight and denser distillate product. A high rate of recycle requires much larger equipment to handle the increased volumetric flow rate, and uses more separation/fractionation energy, and hence more and larger associated energy conservation elements. Further, a high molecular weight oligomer product requires very high temperatures for the fractionation tower bottoms streams that may eliminate the use of simple steam reboilers and require more expensive and complicated fired heaters.

The recycle streams in conventional olefin oligomerization processes are produced in a variety of rather complicated fashions with numerous unit operations, typically including some sort of single stage flash drum providing a very crude separation of reactor product as a means of providing some of the relatively heavy components, followed by various fractionation schemes which may or may not provide sharper separations, and again often providing heavy components as recycle. Further, following the art of olefin oligomerization as it progressed through the 1980s and 1990s, one is directed to introducing various components with the feed to the reaction zone to prolong catalyst cycle life. These additional components further complicate subsequent separation efforts, for example, the addition of hydrogen as disclosed in U.S. Pat. No. 4,544,792 (and in U.S. Pat. No. 4,879,428 noted above, among others). The dense distillate product is generally characterized by a relatively high specific gravity (in excess of 0.775) and a high viscosity, in part due to the composition comprising relatively high levels of aromatics and naphthenes.

Very few references discuss both the merits and methods of producing lighter distillate products, typified by such as jet fuel, kerosene and No. 1 Diesel, via the oligomerization of $C_3$ to $C_8$ olefins. Jet/kero is generally overlooked as a particularly useful middle distillate product, inasmuch as the volume consumed in the marketplace is considerably smaller than its heavier cousins, No. 2 Diesel and No. 4 Diesel (fuel oil). However, jet/kero is a high volume commercial product in its own right, and is also typically suitable as a particular light grade of diesel, called No. 1 Diesel, that is especially useful in colder climates given its tendency to remain liquid and sustain volatility at much lower temperatures. In addition, jet/kero type streams are often blended in with other stocks to produce No. 2 Diesel, both to modify the diesel fuel characteristics, and to allow introduction of otherwise less valuable blendstocks into the final higher value product.

U.S. Pat. No. 4,720,600 discloses an oligomerization process for converting lower olefins to distillate hydrocarbons, especially useful as high quality jet or diesel fuels, wherein an olefinic feedstock is reacted over a shape selective acid zeolite, such as ZSM-5, to oligomerize feedstock olefins and further convert recycled hydrocarbons. The reactor effluent is fractionated to recover a light-middle distillate range product stream and to obtain light and heavy hydrocarbon streams for recycle. The middle distillate product has a boiling range of about 165° C. to 290° C. and contains substantially linear $C_9$ to $C_{16}$ mono-olefinic hydrocarbons, whereas the major portion of the $C_6$ to $C_8$ hydrocarbon components are contained in the lower boiling recycle stream, and the major portion (e.g., 50 wt % to more than 90 wt %) of the $C_{16}+$ hydrocarbon components are contained in the heavy recycle fraction.

According to the present invention, it has now been found that by controlling the ratio of components in the recycle stream, a simpler and more efficient process results to produce fuel products, particularly light distillate products and blendstocks, such as jet fuel, kerosene, and diesel fuel.

SUMMARY OF THE INVENTION

One embodiment of the present invention provides a process for producing a hydrocarbon composition that comprises: (a) contacting a feed stream and an olefinic recycle stream with a molecular sieve catalyst in a reaction zone under olefin oligomerization conditions to produce an oligomerization effluent stream, wherein said feed stream comprises at least one $C_3$ to $C_8$ olefin and said olefinic recycle stream comprises a first olefinic recycle stream (or light olefinic recycle stream) and no more than 10 wt % of $C_{10}+$ non-normal olefins; (b) separating said oligomerization effluent stream to produce a first olefinic stream (or light olefinic stream) and a first hydrocarbon product stream, wherein said first hydrocarbon product stream comprises at least 1 wt % and no more than 30 wt % of $C_9$ non-normal olefin and said light olefinic stream has a weight ratio of $C_4-/(C_5-C_8)$ molecules from about 0.8 to about 1.2 times the weight ratio of $C_4-/(C_5-C_8)$ molecules found in said oligomerization effluent stream; and (c) splitting said light olefinic stream to produce said light olefinic recycle stream and a first purge stream.

One embodiment of the present invention provides a process for producing a hydrocarbon composition that further comprises: (d) separating said first purge stream to produce a second purge stream and a second olefinic stream; and (e) splitting said second olefinic stream to produce a second olefinic recycle stream and a second hydrocarbon product stream, wherein said olefinic recycle stream further comprises at least 1 wt % and no more than 80 wt % of said second olefinic recycle stream based on the total weight of the olefinic recycle stream.

As used herein, the term "olefinic recycle stream" refers to the single or combined individual recycle streams provided along with the feed stream for contacting (a). Such individual streams may be combined in any manner, including as a mixture with the feed stream. However, attributes of the "olefinic recycle stream" refer to that stream which would result if all individual recycle streams were combined excluding the feed stream, regardless of specifically how the individual streams are provided for contacting (a).

In one embodiment of the present invention, the feed stream comprises a mixture of $C_3$ to $C_5$ olefins comprising at least 5 wt % of $C_4$ olefin, which the mixture may comprise at least 40 wt % of $C_4$ olefin and at least 10 wt % of $C_5$ olefin. In one embodiment of the present invention, the feed stream comprises no more than about 10 wt % $C_9+$ hydrocarbons. In one embodiment of the present invention, the feed stream comprises less than 45 wt % saturates. In one embodiment of the present invention, the feed stream comprises no greater than 10 wt % propane. In one embodiment of the present invention, the feed stream comprises no more than 1.0 wt % $C_2$ hydrocarbons. In one embodiment of the present invention, the feed stream comprises a product stream from one or more of an oxygenates to olefins process, a steam cracking process, or a catalytic cracking process. In one embodiment of the present invention, the feed stream contains $C_4$ olefin and the contacting (a) is conducted so as to convert about 80 wt % to about 99 wt % of the $C_4$ olefin in the feed.

In one embodiment of the present invention, the contacting (a) occurs in a boiling water reactor, also referred to as a heat exchanger reactor. In one embodiment of the present invention, the contacting (a) occurs in at least 3 reactors. In one embodiment of the present invention, the olefin oligomerization conditions in said contacting (a) has an olefinic recycle stream to feed stream weight ratio of from about 0.1 to about 3.0, alternatively from about 0.5 to about 2.0, alternatively from about 0.5 to about 1.3. In one embodiment of the present invention, the contacting (a) is conducted at a WHSV of about 0.5 to about 6.0 based on the olefin in the feed stream. In one embodiment of the present invention, the contacting (a) is conducted at a WHSV of about 0.7 to about 9.0 based on the olefin in the combined feed stream and olefinic recycle stream. In one embodiment of the present invention, the contacting (a) is conducted in a reaction zone, alternatively in a plurality of reaction zones in parallel, alternatively connected in series, and the difference between the highest and lowest temperatures within each reaction zone is 40° F. (22° C.) or less. In one embodiment of the present invention, the contacting (a) is conducted at a partial pressure of olefins of at least 400 psig. In one embodiment of the present invention, the contacting (a) occurs in the presence of substantially no hydrogen.

In one embodiment of the present invention, the highest and lowest temperatures within any reaction zone are between about 150° C. and about 350° C. In one embodiment of the present invention, the molecular sieve comprises ZSM-5, ZSM-11, ZSM-12, ZSM-22, ZSM-57 and/or MCM-22. In one embodiment of the present invention, the yield of butane and lighter saturates generated in contacting (a) is less than 2.0 wt %, alternatively less than 1.5 wt %, alternatively less than 1.0 wt %, alternatively less than 0.5 wt %.

In one embodiment of the present invention, the olefinic recycle stream comprises no more than 7 wt % of $C_{10}+$ non-normal olefins, and may have a final boiling point of no greater than 360° F. (182° C.). In one embodiment of the present invention, the olefinic recycle stream comprises no more than 30 wt % of $C_9+$ non-normal olefins, and may have a final boiling point of no greater than 310° F. (154° C.). In one embodiment of the present invention, the olefinic recycle stream comprises at least about 1 wt % to about 50 wt % $C_4$ hydrocarbons. In one embodiment of the present invention, the olefinic recycle stream comprises less than about 20 wt % $C_3-$ hydrocarbons.

In one embodiment of the present invention, the first hydrocarbon product stream comprises between about 2.0 wt % and about 25.0 wt % of $C_9$ non-normal olefin. In one embodiment of the present invention, the first hydrocarbon product stream comprises between about 0.5 wt % and about 12 wt % of $C_{17}$ to $C_{20}$ hydrocarbons. In one embodiment of the present invention, the first hydrocarbon product stream has a final boiling point of less than about 350° F. (177° C.). In one embodiment of the present invention, the first hydrocarbon product stream has an initial boiling point of at least 260° F. (127° C.).

In one embodiment of the present invention, the light olefinic stream contains no more than 7 wt % of $C_{10}+$ non-normal olefins, and may have a final boiling point of no greater than 360° F. (182° C.) and may have an initial boiling point of at least 260° F. (127° C.). In one embodiment of the present invention, the light olefinic stream comprises no more than 30 wt % $C_9+$ non-normal olefins, and may have a final boiling point of no greater than 310° F. (154° C.). In one embodiment of the present invention, the light olefinic stream comprises at least about 2 wt % to about 50 wt % $C_4$ hydrocarbons. In one embodiment of the present invention, the light olefinic stream comprises no greater than about 20 wt % $C_3-$ hydrocarbons.

In one embodiment of the present invention, the separating (b) is conducted in one or more steps, such as in one or more of a flash drum, membrane, and fractional distillation tower. In one embodiment, the separating (b) is conducted in a fractionation tower.

In one embodiment of the present invention, at least 20 wt % of the light olefinic stream generated in splitting (c) is provided as said olefinic recycle stream in contacting (a). In one embodiment of the present invention, at least 20 wt % of said olefinic recycle stream comprises said light olefinic recycle stream based on the total weight of said olefinic recycle stream.

In one embodiment of the present invention, the first hydrocarbon product stream is saturated with hydrogen to produce a saturated product which may comprise at least 80 wt % aliphatic hydrocarbons.

In one embodiment of the present invention, said first purge stream comprises from about 5 wt % to about 80 wt % of said light olefinic stream. In one embodiment of the present invention, said second purge stream is richer in $C_4-$ molecules than the first purge stream. In one embodiment of the present invention, said second purge stream comprises at least about 50 wt % $C_4-$ molecules. In one embodiment of the present invention, the second purge stream comprises at least about 50 wt % $C_4-$ saturates. In one embodiment of the present invention, the second purge stream comprises no greater than 30 wt % $C_5+$ molecules. In one embodiment of the present invention, the second purge stream is in the vapor phase. In one embodiment of the present invention, said second olefinic stream is richer in $C_5-C_8$ molecules than the first purge stream. In one embodiment of the present invention, the second olefinic stream comprises at least about 50 wt % $C_5-C_8$ molecules. In one embodiment of the present invention, the second olefinic stream comprises at least about 10 wt % to about 80 wt % $C_5-C_8$ saturates. In one embodiment of the present invention, the second olefinic stream comprises no greater than about 30 wt % $C_4-$ molecules. In one embodiment of the present invention, the second olefinic stream comprises no greater than about 7.0 wt % $C_{10}+$ non-normal olefins, and may have a final boiling point of no more than about 360° F. (182° C.). In one embodiment of the present invention, the second olefinic stream comprises no greater than about 30 wt % $C_9+$ non-normal olefins, and may have a final boiling point of no more than about 310° F. (154° C.).

In one embodiment of the present invention, said splitting (e) is such that at least about 50 wt % of said second olefinic recycle stream is provided as said olefinic recycle stream in contacting (a). In one embodiment of the present invention, the separating (d) of the first purge stream occurs in one or more steps.

Any two or more of the above embodiments can be combined to describe additional embodiments of the invention of this patent application.

DETAILED DESCRIPTION OF THE EMBODIMENTS

Figure 1:
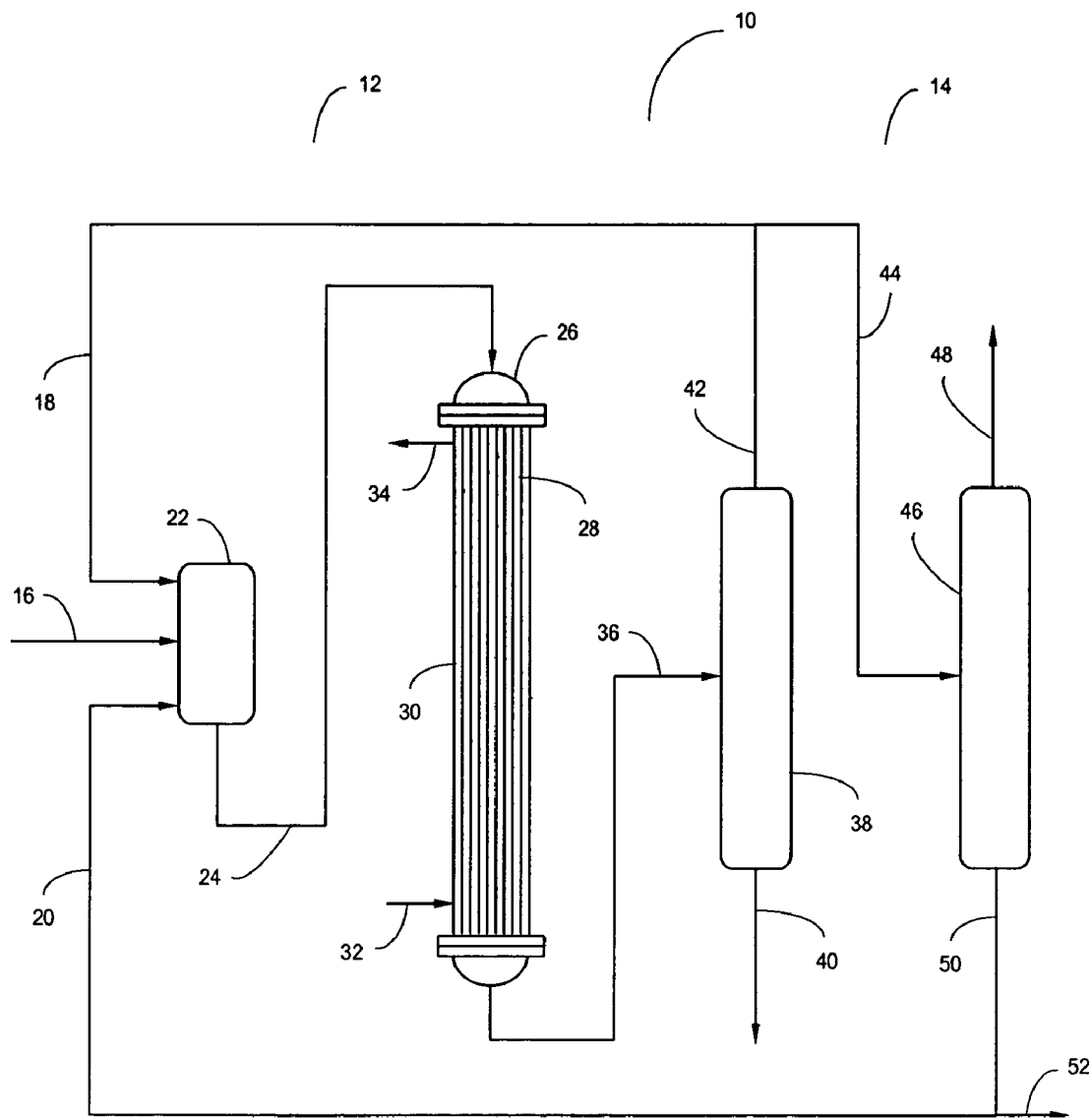
FIG. 1 is a flow diagram of a process for producing a hydrocarbon composition according to one embodiment of the invention.

As used herein, the term "$C_x$ hydrocarbon" indicates hydrocarbon molecules having the number of carbon atoms represented by the subscript "x". The term "$C_x+$ hydrocarbons" indicates those molecules noted above having the number of carbon atoms represented by the subscript "x" or greater. For example, "$C_{10}+$ hydrocarbons" would include $C_{10}$, $C_{11}$ and higher carbon number hydrocarbons. Similarly "$C_x-$ hydrocarbons" indicates those molecules noted above having the number of carbon atoms represented by the subscript "x" or fewer. As used herein, "$C_5-C_8$" means molecules having to 5 to 8 carbons.

Weight Hourly Space Velocity (WHSV) values cited herein are based on the amount of the molecular sieve contained in the olefin oligomerization catalysts without allowing for any binder or matrix that may also be present in the catalyst.

Distillation temperature values cited herein, including initial boiling point and final boiling point (or end point) refer to measurements made in accordance with ASTM Test Method D86, the entire contents of which are incorporated herein by reference.

The term "normal olefin" refers to any olefin that contains a single, unbranched chain of carbon atoms as defined in *Hawley's Condensed Chemical Dictionary*, 14$^{th}$ Edition. Therefore a "non-normal olefin," as used herein, is an olefin that is not a "normal olefin," and would, therefore, contain at least one branched chain of carbon atoms.

The present invention provides a process for oligomerizing a feed containing at least one $C_3$ to $C_8$ olefin together with an olefinic recycle stream containing no more than 10 wt % $C_{10}+$ non-normal olefins over a molecular sieve catalyst such that said olefinic recycle stream to fresh feed stream weight ratio is from about 0.1 to about 3.0, alternatively from about 0.5 to about 2.0, alternatively from about 0.5 to about 1.3, and the difference between the highest and lowest temperatures within the reactor is 40° F. (22° C.) or less. The oligomerization effluent is then separated into a first hydrocarbon product stream and at least one light olefinic stream, also referred to as the first olefinic stream. At least part of the light olefinic stream(s) is recycled to the oligomerization process.

The hydrocarbon product streams are useful as fuel products or blending stocks to produce fuel products, such as Jet Fuel A and No. 1 and No. 2 Diesel. If desired, at least part of the hydrocarbon product streams can be hydrogenated to at least partially saturate the olefins contained therein, and similarly used as fuel products or blendstocks.

Oligomerization Feed

The fresh feed to the oligomerization process can include any single $C_3$ to $C_8$ olefin or any mixture thereof in any proportion. Particularly suitable feeds include mixtures of propylene and butylenes having at least 5 wt %, such as at least 10 wt %, for example, at least 20 wt %, such as at least 30 wt % or at least 40 wt % $C_4$ olefin. Also useful are mixtures of $C_3$ to $C_5$ olefins having at least 40 wt % $C_4$ olefin and at least 10 wt % $C_5$ olefin.

Conveniently, the feed should contain no more than about 1.0 wt %, or even no more than 0.1 wt % of $C_2-$ hydrocarbons, because ethylene is less reactive in the present process than other light olefin, and thus requires substantially more processing to obtain a good ultimate conversion. Further, ethylene and light saturates, such as ethane and methane, are highly volatile, and it will require much more work to recover them in the separation system, likely necessitating the use of expensive and complicated refrigeration systems. It is also of benefit to limit the amount of $C_9+$ hydrocarbons, of any kind, in the feed, to no more than about 10 wt %, or no more than 5 wt %, or even no more than 1 wt %, because $C_9+$ hydrocarbons are useful components of the first hydrocarbon product stream and so it is counter-productive to subject them to the oligomerization process of the invention.

It is also desirable to limit the amount of saturates in the feed, because saturates are not converted in the oligomerization step and tend to accumulate in said olefinic recycle stream, thereby reducing the light olefin content of said olefinic recycle stream. The amount of non-olefins, especially saturates, in the feed should be less than 45 wt %, such as less than 35 wt %, for example, less than 25 wt %, typically less than 15 wt %, or less than 10 wt % or even less than 5 wt %. More particularly, the amount of non-olefins, especially saturates in the feed should be from about 5 wt % to about 45 wt %, from about 10 wt % to about 35 wt %, from about 15 wt % to about 25 wt %. More particularly, the amount of propane can be no greater than about 10 wt %, such as no more than 5 wt %, for example, no more than 1 wt %, or no more than 0.5 wt %. Even more particularly, the amount of propane can be no greater than about 0.5 wt % to about 10 wt % or about 1 wt % to about 5 wt %.

In one embodiment, the olefinic feed is obtained by the conversion of an oxygenate, such as methanol, to olefins over a silicoaluminophosphate (SAPO) catalyst, according to the method of, for example, U.S. Pat. Nos. 4,677,243 and 6,673,978; or an aluminosilicate catalyst, according to the method of, for example, WO04/18089; WO04/16572; EP 0 882 692; and U.S. Pat. No. 4,025,575. Alternatively, the olefinic feed can be obtained by the catalytic cracking of relatively heavy petroleum fractions, or by the pyrolysis of various hydrocarbon streams, ranging from ethane to naphtha to heavy fuel oils, in admixture with steam, in a well understood process known as "steam cracking".

As stated above, the overall feed to the oligomerization process also contains an olefinic recycle stream containing no more than 10 wt % of $C_{10}$+ non-normal olefins. Generally, the olefinic recycle stream should contain no greater than 7.0 wt %, for example, no greater than 5.0 wt %, such as no greater than 2.0 wt %, or no greater than 1.0 wt %, or even no greater than 0.1 wt % of $C_{10}$+ non-normal olefins. The olefinic recycle stream should contain from about 0.1 wt % to about 10.0 wt %, or about 0.5 wt % to about 10.0 wt %, or about 1.0 wt % to about 7.0 wt % of $C_{10}$+ non-normal olefins. Alternatively, the final boiling point temperature of the olefinic recycle stream should be no greater than 360° F. (182° C.), no greater than 340° F. (171° C.), such as no greater than 320° F. (160° C.), for example, no greater than 310° F. (154° C.), or even no greater than 305° F. (152° C.). The final boiling point temperature of the olefinic recycle stream should be in the range of from 300° F. (149° C.) to 360° F. (182° C.), from 305° F. (152° C.) to 340° F. (171° C.), or from 310° F. (154° C.) to 320° F. (160° C.). In one embodiment, the olefinic recycle stream contains no greater than 30.0 wt %, such as, no greater than 25.0 wt %, for example, no greater than 20.0 wt %, or no greater than 15.0 wt %, or no greater than 10.0 wt % of $C_9$+ non-normal olefins. The olefinic recycle stream contains from about 5.0 wt % to about 30.0 wt %, or from about 10 wt % to about 25 wt %, or from about 15 wt % to about 20 wt % of $C_9$+ non-normal olefins. Alternatively, the final boiling point temperature of the olefinic recycle stream should be no greater than 290° F. (143° C.), such as no greater than 275° F. (135° C.), for example, no greater than 260° F. (127° C.). The final boiling point temperature of the olefinic recycle stream should be in the range of from 260° F. (127° C.) to 310° F. (154° C.) or from 275° F. (135° C.) to 290° F. (143° C.).

In one embodiment, the olefinic recycle stream contains at least 1 wt %, at least 5 wt %, at least 10 wt %, at least 15 wt %, or at least 20 wt % $C_4$ hydrocarbons of any species. In one embodiment, the olefinic recycle stream contains no greater than 50 wt %, no greater than 40 wt %, no greater than 30 wt %, or no greater than 25 wt %, or no greater than 20 wt %, or no greater than 10 wt %, or no greater than 5 wt % $C_4$ hydrocarbons (of any species). The olefinic recycle stream contains from about 1 wt % to about 50 wt %, or from about 5 wt % to about 40 wt %, or from about 10 wt % to about 30 wt %, or from about 20 wt % to about 25 wt % $C_4$ hydrocarbons (of any species). Additionally, the olefinic recycle stream may contain no greater than 20 wt %, no greater than 10 wt %, no greater than 5 wt %, or no greater than 2 wt % $C_3$- hydrocarbons, such as propylene or propane. The olefinic recycle stream may contain from about 0.1 wt % to about 20 wt %, or from about 0.5 wt % to about 10 wt %, or from about 1.0 wt % to about 5 wt %, or from about 1.5 wt % to about 2 wt % $C_3$- hydrocarbons, such as propylene or propane. This can be achieved by, for example, employing an additional separation of all or a portion of the olefinic recycle stream generated by a separation device into one stream comprising $C_4$- with only a small amount of $C_5$+ hydrocarbons, and a second debutanized stream as all or a portion of the olefinic recycle stream provided to the oligomerization reactor.

The amount of olefinic recycle stream fed to the oligomerization process is such that said olefinic recycle stream to fresh feed stream weight ratio is from about 0.1 to about 3.0, alternatively from about 0.5 to about 2.0, alternatively from about 0.5 to about 1.3. More particularly, the weight ratio of olefinic recycle stream to fresh olefinic feedstock can be at least 0.1, or at least 0.3, or at least 0.5, or at least 0.7 or at least 0.9, but generally is no greater than 3.0, or no greater than 2.5, or no greater than 2.0, or no greater than 1.8, or no greater than 1.5 or no greater than 1.3. The weight ratio of olefinic recycle stream to fresh olefinic feedstock can be from about 0.1 to about 3.0, or from about 0.3 to about 2.5, or from about 0.5 to about 2.0, or from about 0.7 to about 1.8, or from about 0.9 to about 1.5, or from about 1.0 to about 1.3. As noted previously, the olefinic recycle stream is comprised of one or more substituent recycle streams obtained through various separations described herein, such as light olefinic recycle stream (also referred to as first olefinic recycle stream), or second olefinic recycle stream, or both in combination, or including others derived therefrom.

Oligomerization Process

The oligomerization process of the invention comprises contacting the $C_3$ to $C_8$ olefin feed and the olefinic recycle stream with a molecular sieve catalyst under conditions such that the olefins are oligomerized to produce a hydrocarbon composition conveniently comprising at least 90 wt % of $C_9$ to $C_{20}$ non-normal olefin, non-normal saturates or combinations thereof. Typically the hydrocarbon composition comprises less than 15 wt % of $C_{17}$+ non-normal olefins, and generally less than 15 wt % of $C_{17}$+ hydrocarbons.

The catalyst used in the oligomerization process can include any crystalline molecular sieve which is active in olefin oligomerization reactions. In one embodiment, the catalyst includes a medium pore size molecular sieve having a Constraint Index of about 1 to about 12. Constraint Index and a method of its determination are described in U.S. Pat. No. 4,016,218, which is incorporated herein by reference. Examples of suitable medium pore size molecular sieves are those having 10-membered ring pore openings and include those of the TON framework type (for example, ZSM-22, ISI-1, Theta-1, Nu-10, and KZ-2), those of the MTT framework type (for example, ZSM-23 and KZ-1), of the MFI structure type (for example, ZSM-5), of the MFS framework type (for example, ZSM-57), of the MEL framework type (for example, ZSM-11), of the MTW framework type (for example, ZSM-12), of the EUO framework type (for example, EU-1) and members of the ferrierite family (for example, ZSM-35).

Other examples of suitable molecular sieves include those having 12-membered pore openings, such as ZSM-18, zeolite beta, faujasites, zeolite L, mordenites, as well as members of the MCM-22 family of molecular sieves (including, for example, MCM-22, PSH-3, SSZ-25, ERB-1, ITQ-1, ITQ-2, MCM-36, MCM-49 and MCM-56). Other 10- and 12-member pore ring structure aluminosilicates and their SAPO analogs will also function.

In one preferred embodiment, the molecular sieve catalyst comprises ZSM-5 having a homogeneous crystal size of <0.05 micron and a relatively high activity (alumina content) characterized by a $SiO_2/Al_2O_3$ molar ratio of around 50:1.

The molecular sieve may be supported or unsupported, for example, in powder form, or used as an extrudate with an appropriate binder. Where a binder is employed, the binder is conveniently a metal oxide, such as alumina, and is present in an amount such that the oligomerization catalyst contains between about 2 and about 80 wt % of the molecular sieve.

The oligomerization reaction should be conducted at sufficiently high WHSV of fresh feed to the reactor to ensure the desired low level of $C_{17}+$ oligomers in the reaction product. As used herein, WHSV is based on the weight of the entire catalyst in the reaction zone, for a catalyst that is 65 wt % active molecular sieve and 35 wt % inert binder/filler. (One can thus determine WHSV based on weight of active material in the reaction zone through dividing the values provided herein by 0.65, allowing one to determine the appropriate WHSV for a catalyst comprising any amount of active material used in the present invention. For example, a value of WHSV of 1.0 stated herein would, for a catalyst having 32.5 wt % active material and 67.5 wt % inert binder/filler, be equivalent to a WHSV of 0.5). In general, the reaction should occur at a WHSV of no less than 0.5 or no less than 0.7, or no less than 1.0, or no less than 1.2, or no less than 1.4, or no less than 1.6, or no less than 1.8, or no less than 2.0, or no less than 2.5, or no less than 3.0, or no less than 3.5, or no less than 4.0 based on olefin in the fresh feed to the reactor. The upper level of WHSV is not narrowly defined, but is generally not more than 6.0 or 5.0 based on olefin in the fresh feed to the reactor. Increasing the WHSV beyond these levels may significantly decrease the catalyst/reactor cycle length between regenerations, especially at higher levels of $C_4$ conversion. The reaction should occur at a WHSV of from 0.5 to about 6.0, or from about 0.7 to about 5.0, or from about 1.0 to about 4.0 based on olefin in the fresh feed to the reactor. With regard to the combined fresh olefin feed and recycle to the reactor, the WHSV should be no less than about 0.7, or no less than about 1.0, or no less than about 1.5, or no less than about 1.8, or no less than about 2.2, or no less than about 2.5, or no less than about 3.0 or no less than about 3.5 based on the olefin contained in the combined feed stream and olefinic recycle stream(s) to the reactor. For the same reason, the WHSV for the combined fresh olefin feed and recycle to the reactor should be no more than about 9.0, about 8.0, about 7.0, or about 6.0 based on the olefin contained in the combined feed stream and olefinic recycle stream(s) to the reactor. With regard to the combined fresh olefin feed and recycle to the reactor, the WHSV should be from about 0.7 to about 9.0, or from about 1.0 to about 8.0, or from about 1.5 to about 7.0, or from about 1.8 to about 6.0.

The oligomerization process can be conducted over a wide range of temperatures, although generally the highest and lowest temperatures within the oligomerization reaction zone should be between about 150° C. and about 350° C., such as between about 180° C. and about 330° C., for example, between about 210° C. and 310° C.

It is, however, important to ensure that the temperature across the reaction zone is maintained relatively constant so as to produce the desired level of $C_4$ olefin conversion at a given WHSV and point in the reaction cycle, and to minimize the production (yield) of undesirable butane and lighter saturates from the oligomerization reaction (contacting). Thus, as discussed above, the difference between the highest and lowest temperatures within the reactor should be maintained at about 40° F. (22° C.) or less, such as about 30° F. (17° C.) or less, for example, about 20° F. (11° C.) or less, conveniently about 10° F. (6° C.) or less, or even about 5° F. (3° C.) or less. The difference between the highest and lowest temperatures within the reactor should be maintained from about 1° F. (0.6° C.) to about 40° F. (22° C.), or from about 5° F. (3° C.) to about 30° F. (17° C.), or from about 10° F. (6° C.) to about 20° F. (11° C.).

The oligomerization process can be conducted over a wide range of olefin partial pressures, although higher olefin partial pressures are preferred since low pressures tend to promote cyclization and cracking reactions, and are thermodynamically less favorable to the preferred oligomerization reaction. Typical olefin partial pressures of olefins in the combined feed stream and olefinic recycle stream as total charge to the reactor comprise at least about 400 psig (2860 kPa), such as at least about 500 psig (3550 kPa), for example, at least about 600 psig (4240 kPa), or at least about 700 psig (4930 kPa), or at least about 800 psig (5620 kPa), or even about 900 psig (6310 kPa). Typical olefin partial pressures of olefins in the combined feed stream and olefinic recycle stream as total charge to the reactor are in the range of from about 400 psig (2860 kPa) to about 2000 psig (13,782 kPa), or from about 500 psig (3550 kPa) to about 1500 psig (10,337 kPa), or from about 600 psig (4240 kPa) to about 1200 psig (8269 kPa). It will, of course, be appreciated that the olefin partial pressure will be lower at the exit to the reactor as fewer moles of olefins exist due to the oligomerization reaction.

Typically, the conditions of the oligomerization process are controlled so as ensure that the conversion of $C_4$ olefins in the feed is at least about 80 wt %, or at least about 85 wt % or at least about 90 wt %, or at least about 92 wt %, but no greater than about 99%, or no greater than about 98 wt %, or no greater than about 96 wt %, or no greater than about 94 wt %. The conditions of the oligomerization process are controlled so as to ensure that the conversion of $C_4$ olefins in the feed is in the range of from about 80 wt % to about 99 wt %, or from about 85 wt % to about 98 wt %, or from about 90 wt % to about 96 wt %, or from about 92 wt % to about 94 wt %. During the course of the oligomerization process, the catalyst will lose activity due to the accumulation of carbonaceous deposits and hence the $C_4$ olefin conversion will tend to decline with time. Thus to sustain a given level of $C_4$ olefin conversion, the temperature at which the oligomerization reaction is conducted is continually raised until some limit, discussed above, is reached. At that point, the catalyst is generally regenerated, either in situ or ex situ, by combustion of the coke deposits with oxygen/air using methods and conditions that are well known in the art. The regenerated catalyst may then be used again in the oligomerization reaction at some initial temperature, with the continually increasing temperature cycle being repeated.

The catalyst and the reactor conditions may be selected to achieve a low yield of butane and lighter saturates from the oligomerization reaction, such as no greater than about 2.0 wt %, or no greater than about 1.5 wt %, or no greater than about 1.0 wt % butanes and lighter saturates. The catalyst and the reactor conditions may be selected to achieve a low yield of butane and lighter saturates from the oligomerization reaction in the range of from about 0.1 wt % to about 2.0 wt %, or from about 0.2 wt % to about 1.5 wt % butanes and lighter saturates.

Conveniently, the oligomerization process is conducted in a plurality of serial adiabatic reactors with interstage cooling, such as is disclosed in U.S. Pat. No. 4,560,536, the entire contents of which is incorporated herein by reference. In order to achieve the desired low ΔT within each reactor, more than three reactors, for example, about 4 to 10 reactors, may be required. Conveniently, the reactors employed are boiling water reactors, sometimes called heat exchanger reactors, e.g., such as is discussed in U.S. Pat. Nos. 4,263,141 and 4,369,255 (for methanol production), and "Petroleum Processing, Principles and Applications," R. J. Hengstebeck, McGraw-Hill, 1959, pages 208-218 (specifically for olefin oligomerization, using solid phosphoric acid).

There can be substantially no hydrogen added to the reactor during the oligomerization reaction. There can be substantially no hydrogen in the feed stream to the reactor, and therefore, substantially no hydrogen present in the olefinic recycle streams. "Substantially no hydrogen" means that the hydrogen level in the stream is undetectable by analytical means, such as gas chromatography (GC). If hydrogen is added to the reactor or is present in detectable amounts in the feed stream, there can be no greater than about 0.60 wt %, no greater than about 0.50 wt %, no greater than about 0.40 wt %, no greater than about 0.30 wt %, no greater than about 0.20 wt %, no greater than about 0.10 wt %, no greater than about 0.05 wt %, no greater than about 0.01 wt %, or no greater than about 0.005 wt %, based on the total feed stream to the reactor. If hydrogen is added to the reactor or is present in detectable amounts in the feed stream, there can be a range of from about 0.001 wt % to about 0.60 wt %, or from about 0.005 wt % to about 0.50 wt %, or from about 0.01 wt % to about 0.40 wt %, or from about 0.05 wt % to about 0.30 wt %, or from about 0.10 wt % to about 0.20 wt %, based on the total feed stream to the reactor. If hydrogen is added to the reactor or is present in detectable amounts in the feed stream, and therefore present in the olefinic recycle streams, there can be no greater than about 0.20 wt %, no greater than about 0.18 wt %, no greater than about 0.15 wt %, no greater than about 0.10 wt %, no greater than about 0.05 wt %, no greater than about 0.01 wt %, or no greater than about 0.005 wt %, based on the total feed stream and the olefinic recycle streams to the reactor. If hydrogen is added to the reactor or is present in detectable amounts in the feed stream, and therefore present in the olefinic recycle streams, there can be a range of from about 0.001 wt % to about 0.20 wt %, or from about 0.005 wt % to about 0.18 wt %, or from about 0.01 wt % to about 0.15 wt %, or from about 0.05 wt % to about 0.10 wt %, based on the total feed stream and the olefinic recycle streams to the reactor.

Separation of the Oligomerization Effluent into the First (Light) Olefinic Stream & First Hydrocarbon Product Stream The separation may be conducted in one or more steps, e.g., a series of flash drums, membranes, or fractional distillation towers, whose appropriate products, either singly or in combination, meet the requirement of having no greater than 10 wt % $C_{10}$+ non-normal olefins to be provided as part of the olefinic recycle to the reactor.

One configuration of the present invention will have the oligomerization product provided directly to a fractionation tower to conduct the separation. By "directly" is meant that no other appreciable separation of components in the oligomerization product is conducted that results in a stream provided to the reactor for recycle prior to the oligomerization product being introduced to the fractionation tower, e.g., the oligomerization product may be provided to a flash drum, to reliably let down the pressure of the stream and provide a separate vapor and liquid stream to different parts of a fractionation tower, where the appropriate separation to produce a light olefinic stream, also referred to as first olefinic stream, is conducted; this would still be "direct."

In providing the oligomerization product directly to a fractionation tower, the light olefin stream, or first olefin stream, overhead, which may be a large portion of the overall olefinic recycle stream(s), and the hydrocarbon product bottoms, which is suitable for use without further processing, need only go through one fractionation step prior to subsequent ultimate use, i.e., the desired streams are simultaneously produced and only fractionated once in a single equipment item.

Conditions can be selected, with regard to the feedstock saturates level, the proportion of light olefinic stream, or first olefinic stream, utilized as olefinic recycle stream and the overhead pressure of the fractionation tower, to allow the overhead product of the fractionation tower receiving the oligomerization product to be totally condensed at a temperature (that is, have a "bubble point temperature") of at least about 80° F. (27° C.), or about 90° F. (32° C.), or about 100° F. (38° C.), or about 110° F. (43° C.), or even about 120° F. (49° C.). In most regions in the world, this will allow all of the material to be condensed against cooling water with indirect heat exchange, or even against air at the higher bubble point temperatures, thus avoiding expensive refrigeration. Alternatively, at least 80 or 90 wt % of the overhead product can be condensed at a temperature of at least about 80° F. (27° C.), or about 90° F. (32° C.), or about 100° F. (38° C.), or about 110° F. (43° C.), or even about 120° F. (49° C.). This uses what is called a mixed condenser, where both a vapor and liquid stream are generated as overhead products. Controlling features are the same as for total condensation.

Although the fractionation tower separating the oligomerization product can be operated at a wide range of pressures, an overhead pressure of no greater than about 80 psig (550 kPa), or about 60 psig (413 kPa), or about 40 psig (276 kPa), or about 25 psig (172 kPa), or about 10 psig (69 kPa) is suitable. An overhead pressure of at least about 1 psig (7 kPa) or about 3 psig (21 kPa), is also suitable. The fractionation tower separating the oligomerization product can be operated at an overhead pressure of from about 1 psig (7 kPa) to about 80 psig (550 kPa), or from about 3 psig (21 kPa) to about 60 psig (413 kPa).

The weight ratio of $C_4$ molecules to $C_5$-$C_8$ molecules in the light olefinic stream can be at least about 0.85, or about 0.90, or about 0.95 times and no greater than about 1.05, or about 1.10, or about 1.15 times the weight ratio of $C_4$- molecules to $C_5$-$C_8$ molecules in the oligomerization effluent stream. The weight ratio of $C_4$- molecules to $C_5$-$C_8$ molecules in the light olefinic stream can be in the range of from about 0.85 to about 1.15, or from about 0.90 to about 1.10, or from about 0.95 to about 1.05 times the weight ratio of $C_4$- molecules to $C_5$-$C_8$ molecules in the oligomerization effluent stream. The light olefinic stream can also contain no greater than about 7.0 wt %, about 5.0 wt %, about 2.0 wt %, about 1.0 wt %, or even about 0.1 wt % $C_{10}$+ non-normal olefins. The light olefinic stream can also contain a range of from about 0.1 wt % to about 7.0 wt %, or from about 0.5 wt % to about 5.0 wt %, or from about 1.0 wt % to about 2.0 wt % $C_{10}$+ non-normal olefins. The final boiling point temperature of the light olefinic stream can be no greater than about 360° F. (182° C.), about 340° F. (170° C.), about 320° F. (160° C.), about 310° F. (155° C.), or even about 305° F. (152° C.), ASTM Test Method D86. The initial boiling point of the distillate product can be at least about 260° F. (127° C.), about 280° F. (138° C.), about 300° F. (149° C.), about 320° F. (160° C.), about 340° F. (171° C.), or about 360° F. (182° C.), according to ASTM Test Method D86. The final boiling point temperature of the light olefinic stream can be in the range of from about 300° F. (149° C.) to about 360° F. (182° C.), or from about 305° F. (152° C.) to about 340° F. (171° C.), or from about 310° F. (155° C.) to about 320° F. (160° C.), according to ASTM Test Method D86. The initial boiling point of the distillate product can be in the range of from about 260° F. (127° C.) to about 360° F. (182° C.), or from about 280° F. (138° C.) 340° F. (171° C.), or from about 300° F. (149° C.) to about 320° F. (160° C.) to ASTM Test Method D86.

In addition, the light olefinic stream can also contain no greater than about 30.0 wt %, about 25.0 wt %, about 20.0 wt %, about 15.0 wt %, or about 10.0 wt % $C_9$+ non-normal olefins. The light olefinic stream can also contain in the range of from about 5.0 wt % to about 30.0 wt %, or from about 10.0 wt % to about 25.0 wt %, or from about 15.0 wt % to about 20.0 wt % $C_9+$ non-normal olefins. The final boiling point temperature of the light olefinic stream can be no greater than about 290° F. (143° C.), about 275° F. (135° C.), or about 260° F. (127° C.), according to ASTM Test Method D86. The final boiling point temperature of the light olefinic stream can be in the range of from about 260° F. (127° C.) to about 310° F. (155° C.), or from about 275° F. (135° C.) to about 290° F. (143° C.), according to ASTM Test Method D86.

The light olefinic stream can have at least about 2 wt %, or about 5 wt %, or about 10 wt %, or about 20 wt %, or about 25 wt % $C_4$ hydrocarbons of any species. The light olefinic stream can have a range of from about 2 wt % to about 25 wt %, or from about 5 wt % to about 20 wt %, or from about 10 wt % to about 15 wt % $C_4$ hydrocarbons of any species. The light olefinic stream can work with no greater than about 60 wt %, or about 50 wt %, or about 40 wt %, or about 30 wt %, or about 25 wt %, or about 20 wt %, or about 10 wt %, or about 5 wt % $C_4$ hydrocarbons of any species. In addition, the light olefinic stream can work with no greater than about 20 wt %, or about 10 wt %, or about 5 wt %, or about 2 wt %, or about 1 wt % of $C_3-$ hydrocarbons of any species. The light olefinic stream can work with a range of from about 0.1 wt % to about 20 wt %, or from about 0.1 wt % to about 10 wt %, or from about 1 wt % to about 5 wt % $C_3-$ hydrocarbons of any species.

The light olefinic stream can work with no greater than about 50 wt %, or about 40 wt %, or about 30 wt %, or about 25 wt %, or about 20 wt %, or about 10 wt %, or about 5 wt % $C_4$ hydrocarbons (of any species). The light olefinic stream can work with a range of from about 5 wt % to about 50 wt %, or from about 10 wt % to about 40 wt %, or from about 20 wt % to about 35 wt %, or from about 25 wt % to about 30 wt % $C_4$ hydrocarbons (of any species). In addition, the light olefinic stream can work with no greater than about 20 wt %, or about 10 wt %, or about 5 wt %, or about 2 wt % of $C_3-$ hydrocarbons of any species. The light olefinic stream can work with a range of from about 2 wt % to about 20 wt %, or from about 5 wt % to about 10 wt % of $C_3-$ hydrocarbons of any species. This can be achieved, for example, by selecting a low saturate content feedstock, or employing an additional separation of a portion of the light olefinic stream into a stream comprising $C_4-$ with only a small amount of $C_5+$ hydrocarbons, and using this debutanized stream as a part of the olefinic recycle stream in conjunction with the remaining portion of the light olefinic stream. Also, the extent of conversion of $C_4-$ olefins in the oligomerization reaction zone can control the amount of $C_4-$ hydrocarbons in the light olefinic stream, and selecting a catalyst with very low yield of detrimental byproduct saturate generation.

After being separated from the oligomerization effluent, the light olefinic stream is split into compositionally equivalent streams to form the light olefinic recycle stream, or first olefinic recycle stream, and the first purge stream. Compositionally equivalent, as used herein, is intended to mean merely a physical separation into two or more streams, and not a temperature or chemical separation, such as distillation, fractionation, or other well known means in the art. In contrast, the separations of the oligomerization effluent stream into the first olefinic stream and the first hydrocarbon product stream, and the first purge stream into the second purge stream and the second olefinic stream, result in two streams that are compositionally distinct.

With regard to the second portion of the light olefinic stream, the first purge stream, at least about 5 wt %, or about 10 wt %, or about 20 wt %, or about 35 wt %, or about 50 wt % of the light olefinic stream can be the first purge stream. No greater than about 80 wt % or about 60 wt % of the light olefinic stream can be first purge stream. From about 5 wt % to about 80 wt %, or from about 10 wt % to about 60 wt %, or from about 20 wt % to about 50 wt %, or from about 30 wt % to about 35 wt % of the light (first) olefinic stream can be the first purge stream.

Separation of the First Purge Stream into the Second Olefinic Stream and Second Purge Stream With regard to the separation of the first purge stream into a second olefinic stream and a second purge stream that is richer in $C_4-$ molecules than the first purge stream, the second purge stream can contain at least about 50 wt %, or about 60 wt %, or about 70 wt %, or about 80 wt %, or about 90 wt %, or about 95 wt % $C_4-$ molecules. The second purge stream can contain at least about 50 wt %, or about 60 wt %, or about 70 wt %, or about 80 wt %, or about 90 wt %, or about 95 wt % $C_4-$ saturates. The second purge stream can contain no greater than about 30 wt %, or about 20 wt %, or about 10 wt %, or about 5 wt %, or about 1 wt % $C_5+$ molecules. The second purge stream can contain a range of from about 50 wt % to about 95 wt %, or from about 60 wt % to about 90 wt %, or from about 70 wt % to about 80 wt % $C_4-$ molecules. The second purge stream can contain a range of from about 50 wt % to about 95 wt %, or from about 60 wt % to about 90 wt %, or from about 70 wt % to about 80 wt % $C_4-$ saturates. The second purge stream can contain a range of from about 1 wt % to about 30 wt %, or from about 5 wt % to about 20 wt %, or from about 10 wt % to about 15 wt % $C_5+$ molecules. The second purge stream can be in the vapor phase, and can be utilized as a fuel gas.

With regard to the separation of the first purge into a second olefinic stream that is richer in $C_5-C_8$ molecules than the first purge stream and a second purge stream, the second olefinic stream can contain at least about 50 wt %, or about 60 wt %, or about 70 wt %, or about 80 wt %, or about 90 wt %, or about 95 wt % $C_5-C_8$ molecules. The second olefinic stream can contain at least about 10 wt %, or about 20 wt %, or about 30 wt % $C_5-C_8$ saturates. The second olefinic stream can contain no greater than about 80 wt %, or about 70 wt %, or about 60 wt %, or about 50 wt % $C_5-C_8$ saturates. The second olefinic stream can contain no greater than about 30 wt %, or about 20 wt %, or about 10 wt %, or about 5 wt %, or about 1 wt % $C_4-$ molecules. The second olefinic stream can contain in the range of from about 50 wt % to about 95 wt %, or from about 60 wt % to about 90 wt %, or from about 70 wt % to about 80 wt % $C_5-C_8$ molecules. The second olefinic stream can contain in the range of from about 10 wt % to about 80 wt %, or from about 15 wt % to about 70 wt %, or from about 20 wt % to about 60 wt %, or from about 30 wt % to about 50 wt % $C_5-C_8$ saturates. The second olefinic stream can contain in the range of from about 1 wt % to about 30 wt %, or from about 5 wt % to about 20 wt %, or from about 10 wt % to about 15 wt % $C_4-$ molecules.

The second olefinic stream can also contain no greater than about 7.0 wt %, about 5.0 wt %, about 2.0 wt %, about 1.0 wt %, or even about 0.1 wt % $C_{10}+$ non-normal olefins. The second olefinic stream can also contain in the range of from about 0.1 wt % to about 7.0 wt %, or from about 0.5 wt % to about 5.0 wt %, or from about 1.0 wt % to about 2.0 wt % $C_{10}+$ non-normal olefins. The final boiling point temperature of the second olefinic stream can be no greater than about 360° F. (182° C.), about 340° F. (170° C.), about 320° F. (160° C.), about 310° F. (155° C.), or even about 305° F. (152° C.), according to ASTM Test Method D86. The final boiling point temperature of the second olefinic stream can be in the range of from about 300° F. (149° C.) to about 360° F. (182° C.), or from about 305° F. (152° C.) to about 340° F. (171° C.), or from about 310° F. (155° C.) to about 320° F. (160° C.), according to ASTM Test Method D86.

In addition, the second olefinic stream can also contain no greater than about 30.0 wt %, about 25.0 wt %, about 20.0 wt %, about 15.0 wt %, or about 10.0 wt % $C_9+$ non-normal olefins. The second olefinic stream can also contain a range of from about 5.0 wt % to about 30.0 wt %, or from about 10.0 wt % to about 25.0 wt %, or from about 15.0 wt % to about 20.0 wt % $C_9+$ non-normal olefins. The final boiling point temperature of the second olefinic stream can be no greater than about 290° F. (143° C.), about 275° F. (135° C.), or about 260° F. (127° C.), according to ASTM Test Method D86. The final boiling point temperature of the second olefinic stream can be in the range of from about 260° F. (127° C.) to about 310° F. (155° C.), or from about 275° F. (135° C.) to about 290° F. (143° C.), according to ASTM Test Method D86.

After being separated from the first purge stream, the second olefinic stream is split into compositionally equivalent streams to form the second olefinic recycle stream and the second hydrocarbon product stream. Compositionally equivalent, as used herein, is intended to mean merely a physical separation into two or more streams, and not a temperature or chemical separation, such as distillation, fractionation, or other well known means in the art. Therefore, the description of the second olefinic stream is also the description of the second hydrocarbon product stream.

With regard to the separation of the first purge stream, the separation may be conducted in one or more steps, e.g., a series of flash drums, membranes, or fractional distillation towers, whose appropriate products, either singly or in combination, meet the requirement of providing a stream richer in $C_4-$ molecules than the first purge stream, and a stream richer in $C_5-C_8$ molecules than the first purge stream. One configuration will have the first purge stream provided directly to a fractionation tower to conduct the separation.

By "directly" is meant that no other appreciable separation of components in the first purge stream is conducted that results in producing a stream richer in $C_4-$ molecules than the first purge stream, and a stream richer in $C_5-C_8$ molecules than the first purge stream, prior to the first purge stream being introduced to the fractionation tower, e.g., the first purge stream may be provided to a refrigerated condensor drum to provide a separate vapor and liquid stream to different parts of a fractionation tower, where the appropriate separation to produce a stream richer in $C_4-$ molecules than the first purge stream and a stream richer in $C_5-C_8$ molecules than the first purge stream is conducted; this would still be "direct."

In the present invention, the stream richer in $C_4-$ molecules separated from the first purge stream can be in the vapor phase, in an operation known as a partial condenser. Conditions can be selected, with regard to the feedstock saturates level, the proportion of light olefinic stream utilized as olefinic recycle stream and the overhead pressure of the fractionation tower, to allow at least about 50 wt %, or about 60 wt %, or about 70 wt %, or about 80 wt %, or about 90 wt % of the overhead product to be condensed at a temperature of at least about 80° F. (27° C.), or about 90° F. (32° C.), or about 100° F. (38° C.), or about 110° F. (43° C.), or even about 120° F. (49° C.). In a partial condenser operation, no liquid product is withdrawn, rather all liquid is recycled to the top of the fractionation tower as reflux. Although the fractionation tower can be operated at a wide range of pressures, an overhead pressure of no greater than about 100 psig (689 kPa) or about 80 psig (551 kPa), and an overhead pressure of at least about 20 psig (138 kPa) or about 40 psig (276 kPa), is suitable.

A typical plant fuel gas system, to which the vapor stream richer in $C_4-$ molecules may be directed, operates at around 50-70 psig (345-482 kPa).

Olefinic Recycle Stream

With regard to providing at least a part of the light olefinic stream as at least a part of the olefinic recycle stream, the light olefinic stream is split into compositionally equivalent streams to form the light olefinic recycle stream, or first olefinic recycle stream, and the first purge stream. At least about 20 wt %, or about 40 wt %, or about 60 wt %, or about 80 wt %, or about 90 wt % of the light olefinic stream can be provided to the reaction zone as olefinic recycle stream. The light olefinic stream can be provided to the reaction zone as olefinic recycle stream in the range of from about 20 wt % to about 90 wt %, or from about 40 wt % to about 80 wt %, or from about 50 wt % to about 60 wt % of the light olefinic stream. The light olefinic recycle stream can be at least about 20 wt %, or about 40 wt %, or about 60 wt %, or about 80 wt %, or about 90 wt % of the total olefinic recycle stream(s) provided to the reaction zone. The light olefinic recycle stream can be in the range of from about 20 wt % to about 90 wt %, or from about 40 wt % to about 80 wt %, or from about 50 wt % to about 60 wt % of the total olefinic recycle stream(s) provided to the reaction zone. In fact, it may comprise the entire (100%, i.e., the only) olefinic recycle stream provided to the reaction zone. The light olefinic recycle stream can be mixed with the olefinic feed stream, e.g., in a drum, with the combined stream from the drum then pumped up to the reaction pressure for introduction to the reaction zone.

A portion of the second olefinic stream can be provided to the oligomerization reaction zone as part of the olefinic recycle stream, separately or combined with another substituent stream (e.g., a light olefinic stream), as the second olefinic recycle stream, with the remainder purged from the system as a second hydrocarbon product stream. This prevents excessive $C_5-C_8$ saturate build-up and maintains a desired level of $C_5-C_8$ saturates in the overall system. The second olefinic recycle stream provided to the oligomerization reaction zone as part of the olefinic recycle stream can be at least about 50 wt %, or about 60 wt %, or about 70 wt %, or about 80 wt %, or about 90 wt % of the total second olefinic stream. The second olefinic recycle stream provided to the oligomerization reaction zone as part of the olefinic recycle stream can be in the range of from about 50 wt % to about 90 wt %, or from about 60 wt % to about 80 wt %, or from about 65 wt % to about 70 wt % of the total second olefinic stream.

Hydrocarbon Product Streams

The hydrocarbon composition recovered as the first hydrocarbon product stream in the process of the invention comprises at least about 1.0 wt %, such as at least about 2.0 wt %, such as at least about 3.0 wt %, for example, at least about 4.0 wt %, conveniently at least about 5.0 wt %, or even at least about 10.0 wt % of $C_9$ non-normal olefin. The hydrocarbon composition recovered as the first hydrocarbon product stream in the process of the invention comprises in the range of from about 1.0 wt % to about 10.0 wt %, or from about 2.0 wt % to about 5.0 wt %, or from about 3.0 wt % to about 4.0 wt % of $C_9$ non-normal olefin. Further, the first hydrocarbon product stream comprises no greater than about 30 wt %, for example, no greater than about 25 wt %, conveniently no greater than about 20 wt %, or no greater than about 15 wt % of $C_9$ non-normal olefin. The hydrocarbon composition recovered as the first hydrocarbon product stream in the process of the invention comprises in the range of from about 1.0 wt % to about 30 wt %, or from about 2.0 wt % to about 25.0 wt %, or from about 3.0 wt % to about 20.0 wt % of $C_9$ non-normal olefin.

In general, the first hydrocarbon product stream contains at least about 90 wt %, for example, at least about 92 wt %, such as at least about 95 wt %, or even at least about 97 wt % of Cg to $C_{20}$ non-normal olefins, non-normal saturates or combinations thereof. The first hydrocarbon product stream contains in the range of from about 90 wt % to about 97 wt %, or from about 92 wt % to about 95 wt % of $C_9$ to $C_{20}$ non-normal olefins, non-normal saturates or combinations thereof. Moreover, the first hydrocarbon product stream generally contains at least about 0.5 wt %, or at least about 1.0 wt %, or at least about 2.0 wt %, or even at least about 3.0 wt %, or at least about 5.0 wt % of $C_{17}$ to $C_{20}$ non-normal olefins, but typically no greater than about 12.0 wt %, or no greater than about 10.0 wt %, or no greater than about 8.0 wt %, or no greater than about 6.0 wt %, or even no greater than about 4.0 wt %, or even no greater than about 2.0 wt % of $C_{17}$ to $C_{20}$ non-normal olefins. The first hydrocarbon product stream generally contains in the range of from about 0.5 wt % to about 12.0 wt %, or from about 1.0 wt % to about 10.0 wt %, or from about 2.0 wt % to about 8.0 wt %, or from about 3.0 wt % to about 6.0 wt %, or from about 4.0 wt % to about 5.0 wt % of $C_{17}$ to $C_{20}$ non-normal olefins. $C_{21}$+ hydrocarbons, such as non-normal olefins, may also be present, though typically the content is very low or even undetectable.

The initial boiling point of the first hydrocarbon product stream is typically at least about 260° F. (127° C.), such as at least about 280° F. (138° C.), including at least about 300° F. (149° C.), for example, at least about 320° F. (160° C.), or even at least about 340° F. (171° C.), or even at least about 360° F. (182° C.). The initial boiling point of the first hydrocarbon product stream is typically in the range of from about 260° F. (127° C.) to about 360° F. (182° C.), or from about 280° F. (138° C.) to about 340° F. (171° C.), or from about 300° F. (149° C.) to about 320° F. (160° C.). The final boiling point of the first hydrocarbon product stream is typically no greater than about 350° C., such as no greater than about 330° C., for example, no greater than about 310° C. or even no greater than about 300° C. The final boiling point of the first hydrocarbon product stream is typically in the range of from about 260° C. to about 350° C., or from about 280° C. to about 330° C.

The first hydrocarbon product stream produced by the process of the invention can be used directly as a blending stock to produce jet or diesel fuel. Alternatively, the first hydrocarbon product stream can be hydrogenated, e.g., according to the method of U.S. Pat. Nos. 4,211,640 and 6,548,721, the entire contents of which are incorporated herein by reference, to saturate at least part of the olefins therein and produce a saturated product. The saturated product can contain at least about 80 wt %, or at least about 85 wt %, or at least about 90 wt %, or at least about 95 wt % or at least about 99 wt % aliphatic hydrocarbons. The saturated product can contain in the range of from about 80 wt % to about 99 wt %, or from about 85 wt % to about 95 wt %, or from about 87 wt % to about 90 wt % aliphatic hydrocarbons. All other characteristics of the saturated distillate product in terms of carbon number distribution, non-normal proportions and boiling point ranges will remain largely unchanged from the olefinic product.

Referring now to FIG. 1, there is shown one example of an oligomerization process for producing a hydrocarbon composition according to the invention. The process shown in FIG. 1 employs an oligomerization system 10, comprising heat exchanger reactor and feed system 12 and separation system 14.

Heat exchanger reactor and feed system 10 includes heat exchanger reactor 26 and feed mixing drum 22. Ancillary elements of heat exchanger reactor and feed system 12 that may exist in practical application of the system according to the present invention, within the knowledge of the skilled artisan, have been omitted for the sake of clarity of the present inventive concept. For example, there would be present a pump on the suction of feed mixing drum 22 providing pressurized material to heat exchanger reactor 26, heat exchangers for preheating the pressurized material or cooling the oligomerization effluent stream from heat exchanger reactor 26, and various control valves and instrumentation.

Separation system 14 includes a first fractional distillation column 38 and a second fractional distillation column 46, and again, ancillary elements of separation system 14 that may exist in practical application of the system according to the present invention, within the knowledge of the skilled artisan, have been omitted for the sake of clarity of the present inventive concept. Such ancillary elements would include, for example, overhead condensers, reflux drums and reflux pumps, water removal means associated with the reflux drum bottoms reboilers, product pumps, heat exchangers for cooling product and achieving improved efficiency by preheating pressurized material provided to heat exchanger reactor 26, and various control valves and instrumentation.

A feed stream containing at least one $C_3$ to $C_8$ olefin is provided in line 16 to feed mixing drum 22. In addition, a portion of the light olefinic recycle stream is provided via line 18 as one olefinic recycle stream to feed mixing drum 22, along with the second olefinic recycle stream in line 20. The combined feed stream and olefinic recycle streams are provided as a common stream in line 24 to heat exchanger reactor 26.

Oligomerization catalyst is present within the tubes 28 of heat exchanger reactor 26. Conditions are provided, for example, the pressure and temperature of the combined feed stream and olefinic recycle streams in line 24, the pressure and temperature within heat exchanger reactor 26, and WHSV, among others, such that the oligomerization reaction occurs within tubes 28. The oligomerization reaction generates heat, and the heat passes through tubes 28 to be absorbed by boiling water flowing around the outside of the tubes in shell side 30. The boiling water in shell side 30 is a mixture of steam and liquid water that passes through line 34. Make-up liquid boiler feed water, conveniently at its bubble point at the desired pressure within shell side 30, is provided in line 32. The steam generated in the heat exchanger reactor 26 may be used, for example, to provide heat in fractionation tower reboilers or to make electricity in turbogenerators.

The presence of a quite pure component, such as water, in a boiling state on the shell side 30 provides an almost constant temperature within shell side 30. The temperature of the boiling fluid in shell side 30 must be kept lower than the desired oligomerization reaction temperature within tubes 28, conveniently at least 5° C. lower, such as at least 10° C. lower, including at least 15° C. lower and even at least 20° C. lower, but typically not exceeding 40° C. lower.

The tubes 28, have a small diameter, for example, an outside diameter of less than about 3 inches, conveniently less than about 2 inches, such as less than about 1.7 inches, and an inside diameter commensurate with the desired pressure rating for the inside of the tubes 28. Tubes 28, also may have a relatively long length, such as greater than about 5 meters, including greater than about 7 meters, conveniently greater than about 9 meters.

The oligomerization effluent stream exits heat exchanger reactor 26 through line 36, having a first weight ratio of $C_4$- molecules to $C_5$-$C_8$ molecules, and is provided to first fractional distillation column 38, comprising a feed tray and a number of trays above and below the feed tray sufficient to enable separation of components in the oligomerization reaction product. First fractional distillation column 38 serves to separate the oligomerized effluent stream in line 36 into a light olefinic stream as an overhead product in line 42, and a first hydrocarbon product stream as a bottoms product in line 40. First fractional distillation column 38 is operated such that the light olefinic stream in line 42 has a composition including a second weight ratio of $C_4$- molecules to $C_5$-$C_8$ molecules that is at least 0.80 and no greater than 1.20 times the weight ratio of $C_4$- molecules to $C_5$-$C_8$ molecules found in the oligomerization effluent stream. Further, the light olefinic stream in line 42 contains no greater than 10 wt % $C_{10}$+ olefinic hydrocarbon molecules, and the first hydrocarbon product stream in line 40 contains at least 1 and no greater than 30 wt % $C_9$ non-normal hydrocarbons. Such a separation is readily effected through proper selection of, for example, the number of trays, the reboiler duty, the condensor duty and rate of reflux, in first fractional distillation column 38.

The light olefinic stream in line 42 is split into two streams. A first portion of the light olefinic stream is provided in line 18, as the light olefinic recycle stream, to feed mixing drum 22, and is then provided to heat exchange reactor 26. A second portion of the light olefinic stream, a first purge stream, is provided in line 44 to second fractional distillation tower 46.

Second fractional distillation column 46 serves to separate the first purge stream in line 44 into a stream richer in $C_4$- molecules than the light olefinic stream (and the first purge stream) as a second purge stream in line 48, and a stream richer in $C_5$-$C_8$ molecules than the light olefinic stream (and the first purge stream) as a second olefinic stream in line 50. Such a separation is readily effected through proper selection of, for example, the number of trays, the reboiler duty, the condensor duty and rate of reflux, in second fractional distillation column 46. The stream richer in $C_5$-$C_8$ molecules than the light olefinic stream, the second olefinic stream, in line 50 is split into two streams. A first portion of the second olefinic stream is provided via line 20 as a second olefinic recycle stream to feed mixing drum 22, and is then provided to heat exchanger reactor 26. A second portion of the second olefinic stream, the second hydrocarbon product stream, is purged from the system via line 52, and may be subjected to further processing to create valuable chemicals or utilized as fuel.

The invention will now be more particularly described with reference to the following examples.

EXAMPLES

Example 1

Olefinic feedstock and recycle materials were prepared as shown in Table 1 and were oligomerized over a catalyst comprising 65 wt % of 0.02 to 0.05 micron crystals of ZSM-5 having a $SiO_2/Al_2O_3$ molar ratio of 50:1, and 35 wt % of an alumina binder. The catalyst was in the form of 1/16 inch extrudates and about 90 cc of catalyst was blended with about 202 cc of inert, silicon carbide beads to reduce the heat generation per unit volume of reaction and placed in the reaction bed of a tubular reactor equipped with a heat management system that allowed the oligomerization reaction to proceed under near isothermal conditions.

TABLE 1

| | Charge A | | Charge B | |
|---|---|---|---|---|
| | Feed | Recycle | Feed | Recycle |
| | Wt. % | | | |
| | 49.52 | 50.48 | 41.84 | 58.16 |
| | Proportion | | | |
| Comp. Wt. % | 1 | 1.02 | 1 | 1.39 |
| Ethane | 0.00 | 0.00 | 0.00 | 0.00 |
| Ethylene | 0.00 | 0.00 | 0.00 | 0.00 |
| Propane | 0.00 | 0.00 | 0.01 | 0.00 |
| Propene | 0.00 | 0.00 | 0.00 | 0.00 |
| iso-butane | 7.24 | 0.10 | 0.99 | 0.02 |
| n-butane | 0.08 | 0.00 | 11.61 | 0.03 |
| t-butene-2 | 0.00 | 0.10 | 27.17 | 0.03 |
| butene-1 | 72.28 | 0.00 | 16.31 | 0.00 |
| iso-butene | 2.88 | 0.00 | 2.65 | 0.01 |
| c-butene-2 | 0.01 | 0.00 | 20.14 | 0.00 |
| iso-pentane | 0.01 | 0.09 | 0.80 | 0.04 |
| n-pentane | 1.72 | 0.00 | 1.56 | 0.04 |
| 1,3-butadiene | 0.00 | 0.00 | 0.05 | 0.00 |
| C5 olefins | 15.75 | 0.10 | 17.28 | 0.15 |
| C6 sats | 0.00 | 0.00 | 0.17 | 0.00 |
| C6 olefins | 0.02 | 0.54 | 1.24 | 1.27 |
| C7 olefins | 0.00 | 1.30 | 0.00 | 3.20 |
| n-heptane | 0.00 | 8.13 | 0.00 | 10.65 |
| C8 olefins | 0.00 | 73.71 | 0.00 | 55.56 |
| C9 olefins | 0.00 | 15.14 | 0.00 | 27.68 |
| C10 olefins | 0.00 | 0.79 | 0.00 | 1.31 |
| Total | 100.00 | 100.00 | 100.00 | 100.00 |

Over the course of this first experimental run, various charges were provided to the reactor to test performance under various conditions over an extended period of time. As the experimental run progressed, the catalyst activity declined, requiring an increase in reactor temperature later in the run to achieve a given conversion of feedstock olefins. In two particular experiments, the feedstock and recycle materials were blended in the proportions shown in Table 1, and the single blended stream ("Charge") was provided to the reactor at 1000 psig (6891 kPa) and other conditions shown in Table 2; wherein the WHSV was based on the olefin in the total charge (combined feed and recycle) and the total catalyst composition (ZSM-5 and binder). Four thermocouples were available, positioned evenly through the reaction bed in the reactor, with one very near the first point where the charge and catalyst come into contact, and one very near the outlet of the reaction bed. The difference between the highest and lowest temperatures within the reactor was from 2 to 7° C. The reaction product was analyzed with a gas chromatograph, and the composition of the products is provided in Table 2. No products having a carbon number greater than 21 were detected.

TABLE 2

| | Experiment (ca. Days On Stream) | |
|---|---|---|
| | 23 | 59 |
| | Charge | |
| | A | B |
| | Reactor T (° C.) | |
| | 235 | 274 |
| | WHSV (1/hr) | |
| Product Comp. Wt. % | 4.2 | 3.9 |
| Ethane | 0.00 | 0.00 |
| Ethylene | 0.00 | 0.00 |
| Propane | 0.01 | 0.01 |
| Propene | 0.06 | 0.05 |
| iso-butane | 3.56 | 0.46 |
| n-butane | 0.14 | 4.33 |
| t-butene-2 | 1.97 | 0.66 |
| butene-1 | 0.58 | 0.22 |
| iso-butene | 0.21 | 0.25 |
| c-butene-2 | 1.26 | 0.43 |
| iso-pentane | 0.10 | 0.41 |
| n-pentane | 0.06 | 0.58 |
| 1,3-butadiene | 0.00 | 0.00 |
| C5 olef | 1.63 | 1.51 |
| C6 sats | 0.06 | 0.11 |
| C6 olefins | 0.93 | 1.00 |
| C7 olefins | 1.61 | 2.34 |
| n-heptane | 4.62 | 6.63 |
| C8 olefins | 40.21 | 29.76 |
| C9 olefins | 15.78 | 18.99 |
| C10 olefins | 2.81 | 3.95 |
| C11 olefins | 2.52 | 3.16 |
| C12 olefins | 12.42 | 12.12 |
| C13-C15 olefins | 4.29 | 6.49 |
| C16 olefins | 4.38 | 4.91 |
| C17-C20 olefins | 0.81 | 1.62 |
| Total | 100.00 | 100.00 |

Example 2

The same apparatus and procedure as Example 1 was utilized for a second, extended experimental run with a fresh batch of catalyst and another set of charge compositions as shown in Table 3. The olefinic feedstocks shown in Table 3 were produced by reacting methanol over a SAPO-34 catalyst generally according to the method of U.S. Pat. No. 6,673,978, with separation of the methanol reaction products to provide a $C_4+$ olefin composition. Over 90 wt % of the olefins in each feed composition were normal in atomic configuration, and the feed composition further contained about 1000 wppm oxygenates, such as methanol and acetone (not shown in Table 3), and 1000 ppm dienes. Some minor adjustments of some components in the feed compositions were made by additions of reagent grade materials to test certain aspects of the operation.

The olefinic recycle compositions shown in Table 3 were produced by taking accumulated batches of the reaction products from the first and this second experimental run and periodically providing those batches to a fractionation tower to separate a distillate product from a light olefinic recycle material, collecting those fractionated materials, and using the fractionated light olefinic recycle material for subsequent experiments. Over 90 wt % of the olefins in each recycle composition were non-normal in atomic configuration. Some minor adjustments of some components in the recycle compositions were made via addition of reagent grade materials to account for unavoidable losses in the fractionation step and test certain other aspects of the operation.

TABLE 3

| | Charge C | | Charge D | | Charge E | | Charge F | |
|---|---|---|---|---|---|---|---|---|
| | Feed | Recycle | Feed | Recycle | Feed | Recycle | Feed | Recycle |
| Wt. % | 38.31 | 61.69 | 45.45 | 54.55 | 49.72 | 50.28 | 47.62 | 52.38 |
| Proportion | 1 | 1.61 | 1 | 1.20 | 1 | 1.01 | 1 | 1.10 |
| Comp. Wt. % | | | | | | | | |
| Butane | 2.02 | 16.62 | 2.29 | 9.99 | 2.80 | 9.28 | 2.13 | 7.53 |
| Butenes | 63.50 | 3.05 | 64.35 | 2.69 | 64.55 | 2.97 | 64.93 | 3.09 |
| Dienes | 0.10 | 0.00 | 0.09 | 0.00 | 0.08 | 0.00 | 0.06 | 0.00 |
| Pentane | 0.54 | 4.72 | 1.75 | 0.19 | 1.37 | 0.97 | 1.50 | 1.85 |
| Pentenes | 21.75 | 1.69 | 20.84 | 2.25 | 20.69 | 2.49 | 21.09 | 2.25 |
| Hexanes | 0.25 | 0.13 | 0.26 | 0.13 | 0.18 | 0.29 | 0.17 | 0.54 |
| Hexenes | 11.81 | 1.27 | 10.40 | 3.10 | 10.31 | 3.52 | 10.10 | 4.29 |
| Heptenes | 0.01 | 2.98 | 0.01 | 3.37 | 0.01 | 3.24 | 0.01 | 3.39 |
| n-Heptane | 0.00 | 6.63 | 0.00 | 7.46 | 0.00 | 7.64 | 0.00 | 8.05 |
| Octenes | 0.02 | 44.09 | 0.01 | 49.63 | 0.01 | 48.90 | 0.01 | 52.84 |
| Nonenes | 0.00 | 18.64 | 0.00 | 20.99 | 0.00 | 20.52 | 0.00 | 16.17 |
| Decenes | 0.00 | 0.18 | 0.00 | 0.20 | 0.00 | 0.19 | 0.00 | 0.00 |
| Total | 100.00 | 100.00 | 100.00 | 100.00 | 100.00 | 100.00 | 100.00 | 100.00 |

For a number of particular experiments using the charge material and proportions shown in Table 3, the butylene conversion and yield of $C_{10}+$ material in the reactor product for each of the charge compositions under a variety of temperatures and approximate days on stream are provided in Table 4. In all of the experiments shown in Table 4, the total reactor pressure was about 1000 psig (7000 kPa), the WHSV was between 3.5 and 4.0 based on the olefin in the total charge combined feed and recycle) and the total catalyst composition (ZSM-5 and binder), and the difference between the highest and lowest temperatures within the reactor was 10° C. or less.

TABLE 4

| Experiment (Days on Stream) | Charge | Reactor T (° C.) | C4= conversion (wt. %) | C10+ yield (wt. %) |
|---|---|---|---|---|
| 2 | C | 207 | 93.3 | 38.0 |
| 3 | C | 212 | 97.9 | 43.4 |
| 5 | C | 211 | 91.9 | 36.0 |
| 8 | C | 211 | 87.9 | 32.1 |
| 13 | D | 221 | 98.4 | 46.3 |
| 14 | D | 220 | 96.3 | 41.6 |
| 15 | D | 220 | 95.5 | 40.2 |
| 17 | D | 220 | 92.4 | 37.1 |
| 20 | E | 225 | 95.6 | 40.1 |
| 24 | E | 227 | 94.6 | 38.3 |
| 32 | E | 233 | 95.1 | 37.4 |
| 41 | E | 244 | 96.2 | 37.6 |
| 46 | E | 247 | 96.2 | 37.5 |
| 51 | E | 253 | 97.2 | 38.7 |
| 55 | F | 252 | 94.9 | 33.0 |
| 57 | F | 255 | 96.0 | 33.5 |
| 59 | F | 259 | 97.0 | 37.0 |
| 62 | F | 259 | 96.8 | 36.0 |

Example 3

Several batches of distillate materials were produced from the fractionation of various batches of reactor product obtained in the first and second experimental runs. The carbon number distribution of those distillate material batches, via the Linear Paraffin GC method, are provided in Table 5. Distillates 1 and 2 in Table 5 were obtained from fractionation operations using the aggregate reactor product from the first experimental run, while Distillate 3 was obtained from fractionation operations of the aggregate reactor product from Charges C, D, and E of the second experimental run. All of the distillate materials contain all of the $C_{11}+$ and almost all of the $C_{10}$ material present from the reaction products, i.e., no separation of any components heavier than $C_{11}$ was conducted on the reactor product in obtaining the distillate materials. As obtained directly from the reactor product via the fractionation tower, all the distillate materials are over 90 wt % non-normal olefin, and further contain very low amounts of aromatics (<100 wppm).

Example 4

The batches of distillate materials obtained in Example 3 were hydrogenated in discrete batches by reacting them with hydrogen over a hydrogenation catalyst. Distillates 1 and 2 were hydrogenated over a nickel-containing catalyst while Distillate 3 was hydrogenated over a palladium-containing catalyst, each according to operations and conditions well known. The carbon number distribution of the distillates are provided in Table 5 and in Table 5A. Hydrogenation did not significantly change the non-normal character of distillate compositions although, following hydrogenation, the distillate materials were almost completely aliphatic. No products having a carbon number greater than 21 were detected. Table 5 provides the carbon number distribution according to the Linear Paraffin GC method, which defines carbon number between two adjacent linear paraffins and integrates each normal peak separately.

In Table 5A the carbon distribution of the non-hydrogenated distillate samples is given. It gives the carbon or isomer distribution. Cn is then defined as all isomers with carbon number "n". With the linear paraffin method what is defined as Cn can contain, e.g., a Cn−1 or Cn+1 isomer due to overlapping GC peaks. As a result, there are differences between the carbon distribution in Table 5 and 5A for the same distillate samples.

The GC analysis data for both Table 5 and 5A were collected on a PONA (Paraffin, Olefin, Naphthene, Aromatic) Gas Chromatograph. On this GC, the distillate sample, prior to entering the GC separation column, is coinjected with hydrogen across a small reactor bed containing saturation catalyst. All the olefinic material in the distillate sample to the GC separation column is thus saturated (if not yet saturated before by hydrogenation). However, it is believed that the carbon number distribution (CND) measured herein are accurate.

TABLE 5

| | Distillate | | |
|---|---|---|---|
| | 1 | 2 | 3 |
| | Before and after hydrogenation | | |
| Comp (wt. %) | | | |
| C4-C7 | 0.06 | 0.18 | 0.06 |
| C8 | 0.05 | 0.57 | 0.10 |
| C9 | 4.80 | 19.32 | 12.58 |
| C10 | 8.66 | 9.24 | 12.59 |
| C11 | 16.24 | 13.05 | 14.30 |
| C12 | 31.99 | 26.71 | 22.84 |
| C13 | 12.78 | 11.61 | 11.65 |
| C14 | 5.72 | 4.96 | 6.92 |
| C15 | 8.13 | 5.92 | 7.66 |
| C16 | 5.78 | 4.47 | 5.29 |
| C17 | 2.15 | 1.81 | 2.53 |
| C18 | 1.46 | 1.03 | 1.73 |
| C19 | 1.24 | 0.73 | 1.07 |
| C20 | 0.96 | 0.39 | 0.70 |
| Total | 100.00 | 99.99 | 100.00 |
| % normal paraffins | 3.17 | 3.49 | 2.75 |

TABLE 5A

| | Distillate | | |
|---|---|---|---|
| | 1 | 2 | 3 |
| | Before hydrogenation | | |
| Comp (wt. %) | | | |
| C4-C7 | 0.25 | 0.42 | 0.68 |
| C8 | 0.35 | 0.95 | 1.03 |
| C9 | 4.94 | 19.76 | 13.25 |
| C10 | 8.69 | 9.35 | 12.95 |
| C11 | 8.46 | 7.45 | 8.11 |
| C12 | 39.13 | 32.44 | 29.17 |
| C13-C15 | 16.72 | 14.87 | 15.99 |
| C16 | 15.85 | 11.16 | 13.80 |
| C17-C20 | 5.61 | 3.59 | 5.01 |
| Total | 100.0 | 100.0 | 100.0 |

Table 6 provides composition and other physical and fuel performance properties of the hydrogenated distillate materials.

TABLE 6

| | Distillate | | | |
|---|---|---|---|---|
| | 1 | 2 | 3 | |
| | After hydrogenation | | | |
| Distillation T10 (° C.) | 188 | 165 | 171 | ASTM D86 |
| Distillation T90 (° C.) | 265 | 250 | 269 | ASTM D86 |
| Distillation End Point (° C.) | 304 | 293 | 308 | ASTM D86 |
| Flash Point (° C.) | 57 | 42 | 47 | ASTM D94 |
| Density @ 15° C. (kg/l) | 0.767 | 0.756 | 0.765 | ISO 12185 |
| Viscosity @ 40° C. (mm2/s) | 1.53 | 1.26 | 1.42 | ASTM D445 |
| Viscosity @ 20° C. (mm2/s) | 2.16 | 1.72 | | ASTM D445 |
| Viscosity @ −20° C. (mm2/s) | 6.06 | 4.15 | | ASTM D445 |
| Freeze Point (° C.) | −56 | −62 | <−50 | ASTM D2386 |
| Aromatics (wppm) | 25 | | 49 | Ultra-violet |
| Sulfur (wppm) | <0.1 | <0.1 | <0.1 | ASTM D2622 |
| Olefins (wt. %) | <0.01 | <0.01 | <0.01 | ASTM D2710 |

Example 5

An oligomerization system is operated according to the method of the present invention as embodied in FIG. 1. Table 7, below, provides the material flows of key streams in the system. Olefinic feed stream in line 16 is provided from a methanol to olefins reaction, using a SAPO-34 catalyst, and associated olefin recovery system. Such a source will leave a small amount of oxygenates in the olefinic feed stream. Oxygen from the oxygenates is almost completely converted to water in the oligomerization reaction, and will exit with the oligomerization effluent stream in line 36. The remaining carbon and hydrogen in the oxygenates almost completely incorporates into the hydrocarbons in the oligomerization effluent stream exiting in line 36.

The overhead pressure of first fractionation tower 38 is 23.2 psia, and the overhead temperature is 131° F., which is approximately the bubble point temperature of the light olefinic stream in line 42 (having the composition in lines 18 and 44); the location of these conditions would be in the reflux drum after the overhead condenser of first fractionation tower 38 (neither of which are shown). The overhead pressure of the second fractionation tower 46 is 89.2 psia, and the overhead temperature is 131° F., conditions at which the second purge stream in line 48 will be a vapor product, but still providing a liquid to utilize as tower reflux; the location of these conditions would be in the reflux drum after the overhead condenser of second fractionation tower 46 (neither of which are shown), in a partial condensor operation.

TABLE 7

| Component Flow* (lbs/hr.) | Stream No. | | | | | | | |
|---|---|---|---|---|---|---|---|---|
| | 16 | 18 | 20 | 36 | 40 | 44 | 48 | 52 |
| Water** | 0.00 | 75.71 | 0.00 | 156.19 | 0.00 | 23.06 | 23.06 | 0.00 |
| Ethene | 0.00 | 1.96 | 0.00 | 2.56 | 0.00 | 0.60 | 0.60 | 0.00 |
| Ethane | 0.00 | 3.94 | 0.00 | 5.14 | 0.00 | 1.20 | 1.20 | 0.00 |
| Propene | 46.19 | 120.63 | 0.00 | 157.38 | 0.00 | 36.75 | 36.75 | 0.00 |
| Propane | 4.21 | 72.54 | 0.00 | 94.63 | 0.00 | 22.09 | 22.09 | 0.00 |
| Butadiene | 94.60 | 0.00 | 0.00 | 0.00 | 0.00 | 0.00 | 0.00 | 0.00 |
| Butenes | 59,851.58 | 3,913.35 | 2.11 | 5,105.39 | 0.00 | 1,192.05 | 1,189.42 | 0.51 |
| Butanes | 2,287.29 | 8,408.58 | 2.74 | 10,970.20 | 0.00 | 2,561.36 | 2,557.94 | 0.67 |
| Pentenes | 19,537.55 | 2,621.19 | 638.85 | 3,419.63 | 0.00 | 798.45 | 3.18 | 156.42 |
| Pentanes | 694.12 | 14,330.94 | 3,493.87 | 18,697.90 | 0.00 | 4,365.38 | 16.07 | 855.44 |
| Hexenes | 8673.66 | 1,643.24 | 402.10 | 2,143.79 | 0.00 | 500.55 | 0.00 | 98.45 |
| Hexanes | 660.83 | 12,906.49 | 3,158.22 | 16,839.43 | 0.00 | 3,931.48 | 0.00 | 773.26 |
| Heptenes | 2166.85 | 3,815.68 | 933.70 | 4,978.00 | 0.01 | 1,162.30 | 0.00 | 228.61 |
| Heptanes | 2.61 | 43.24 | 10.58 | 56.42 | 0.00 | 13.17 | 0.00 | 2.59 |
| Octenes | 587.31 | 56,072.46 | 13,720.94 | 73,344.27 | 191.27 | 17,080.37 | 0.00 | 3359.43 |
| Nonenes | 0.00 | 20,092.39 | 4,916.61 | 42,851.93 | 16,638.98 | 6,120.39 | 0.00 | 1203.78 |
| Decenes | 0.00 | 619.13 | 151.50 | 7,895.75 | 7,087.99 | 188.59 | 0.00 | 37.09 |
| Undecenes | 0.00 | 4.56 | 1.11 | 6,315.06 | 6,309.08 | 1.39 | 0.00 | 0.27 |
| Dodecenes | 0.00 | 0.06 | 0.01 | 27,029.14 | 27,029.06 | 0.02 | 0.00 | 0.00 |
| Tridecenes | 0.00 | 0.00 | 0.00 | 8,505.61 | 8,505.61 | 0.00 | 0.00 | 0.00 |
| Tetradecenes | 0.00 | 0.00 | 0.00 | 3,148.33 | 3,148.33 | 0.00 | 0.00 | 0.00 |
| Pentadecenes | 0.00 | 0.00 | 0.00 | 1,094.99 | 1,094.99 | 0.00 | 0.00 | 0.00 |
| Hexadecenes | 0.00 | 0.00 | 0.00 | 9,424.87 | 9,424.87 | 0.00 | 0.00 | 0.00 |
| Heptadecenes | 0.00 | 0.00 | 0.00 | 1,719.34 | 1,719.34 | 0.00 | 0.00 | 0.00 |
| Octadecenes | 0.00 | 0.00 | 0.00 | 827.41 | 827.41 | 0.00 | 0.00 | 0.00 |
| Nonadecenes | 0.00 | 0.00 | 0.00 | 259.99 | 259.99 | 0.00 | 0.00 | 0.00 |
| Eicosenes | 0.00 | 0.00 | 0.00 | 98.68 | 98.68 | 0.00 | 0.00 | 0.00 |
| Coke+ | 0.00 | 0.00 | 0.00 | 1,815.90+ | 0.00 | 0.00 | 0.00 | 0.00 |
| Methanol | 65.99 | 0.00 | 0.00 | 0.00 | 0.00 | 0.00 | 0.00 | 0.00 |
| Dimethyl Ether | 82.19 | 0.00 | 0.00 | 0.00 | 0.00 | 0.00 | 0.00 | 0.00 |
| Methyl Ethyl Ether | 30.79 | 0.00 | 0.00 | 0.00 | 0.00 | 0.00 | 0.00 | 0.00 |

TABLE 7-continued

| Component Flow* (lbs/hr.) | Stream No. | | | | | | | |
|---|---|---|---|---|---|---|---|---|
| | 16 | 18 | 20 | 36 | 40 | 44 | 48 | 52 |
| Acetone | 5.31 | 0.00 | 0.00 | 0.00 | 0.00 | 0.00 | 0.00 | 0.00 |
| Methyl Acetate | 0.75 | 0.00 | 0.00 | 0.00 | 0.00 | 0.00 | 0.00 | 0.00 |
| TOTAL | 94,791.83 | 124,746.09 | 27,432.34 | 246,957.93 | 82,335.60 | 37,999.20 | 3,850.31 | 6,716.52 |

*Material balance may be in slight error on some components due to round-off and recycle calculation convergence tolerances.
**57.42 lb/hr of water is removed as an aqueous phase from the overhead system of first distillation column 38.
⁺Coke (surrogate molecule: bicyclohexyl) actually accumulates on the catalyst in the reactor rather than passing through line 36.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A process for producing a hydrocarbon composition, said process consisting essentially of:
   a. contacting a feed stream and an olefinic recycle stream with a molecular sieve catalyst in a reaction zone under olefin oligomerization conditions to produce an oligomerization effluent stream, wherein said feed stream comprises at least one $C_3$ to $C_8$ olefin and said olefinic recycle stream comprises a first olefinic recycle stream and no more than about 10 wt % of $C_{10}$+ non-normal olefins;
   b. separating said oligomerization effluent stream to produce a first olefinic stream and a first hydrocarbon product stream comprising jet fuel and diesel fuel, wherein said first hydrocarbon product stream comprises at least about 1 wt % and no more than about 30 wt % of $C_9$ non-normal olefin and said first olefinic stream has a weight ratio of $C_4$-/($C_5$-$C_8$) molecules from about 0.8 to about 1.2 times the weight ratio of $C_4$-($C_5$-$C_8$) molecules found in said oligomerization effluent stream; and
   c. splitting said first olefinic stream to produce said first olefinic recycle stream and a first purge stream.

2. The process of claim 1 further comprising the steps of:
   d. separating said first purge stream to produce a second purge stream and a second olefinic stream; and
   e. splitting said second olefinic stream to produce a second olefinic recycle stream and a second hydrocarbon product stream, wherein said olefinic recycle stream further comprises at least about 1 wt % and no more than about 80 wt % of said second olefinic recycle stream based on the total weight of said olefinic recycle stream.

3. The process of claim 1 wherein said feed stream comprises a mixture of $C_3$ to $C_5$ olefins comprising at least about 5 wt % of $C_4$ olefin.

4. The process of claim 3 wherein said mixture comprises at least about 40 wt % of $C_4$ olefin and at least about 10 wt % of $C_5$ olefin.

5. The process of claim 1 wherein said feed stream comprises no more than about 10 wt % $C_9$+ hydrocarbons.

6. The process of claim 1 wherein said feed stream comprises less than about 45 wt % saturates.

7. The process of claim 1 wherein said feed stream comprises no greater than about 10 wt % propane.

8. The process of claim 1 wherein said feed stream comprises no more than about 1.0 wt % $C_2$ hydrocarbons.

9. The process of claim 1 wherein said feed stream comprises a product stream from one or more of an oxygenate to olefins process, a steam cracking process, or a catalytic cracking process.

10. The process of claim 1 wherein said feed stream contains $C_4$ olefin and said contacting (a) is conducted so as to convert about 80 wt % to about 99 wt % of the $C_4$ olefin in said feed stream.

11. The process of claim 1 wherein said olefin oligomerization conditions in said contacting (a) has an olefinic recycle stream to feed stream weight ratio of about 0.1 to about 3.0.

12. The process of claim 1 wherein said contacting (a) is conducted at a WHSV of about 0.5 to about 6.0 based on the olefin in said feed stream.

13. The process of claim 1 wherein said contacting (a) is conducted at a WHSV of about 1.5 to about 9.0 based on the olefin in the combined feed stream and olefinic recycle stream.

14. The process of claim 1 wherein the highest and lowest temperatures within the reaction zone are between about 150° C. and about 350° C.

15. The process of claim 1 wherein said contacting (a) is conducted at a difference between the highest and lowest temperatures within said reaction zone of about 40° F. (22° C.) or less.

16. The process of claim 1 wherein yield of butane and lighter saturates generated in contacting (a) is less than about 2.0 wt %.

17. The process of claim 1 wherein said contacting (a) occurs in the presence of substantially no hydrogen.

18. The process of claim 1 wherein said olefinic recycle stream comprises no more than about 7 wt % of $C_{10}$+ non-normal olefins.

19. The process of claim 1 wherein said olefinic recycle stream comprises no more than about 30 wt % of $C_9$+ non-normal olefins.

20. The process of claim 1 wherein said olefinic recycle stream comprises at least about 1 wt % to about 50 wt % $C_4$ hydrocarbons.

21. The process of claim 1 wherein said olefinic recycle stream comprises less than about 20 wt % $C_3$- hydrocarbons.

22. The process of claim 1 wherein said first hydrocarbon product stream comprises between about 2.0 wt % and about 25.0 wt % of $C_9$ non-normal olefin.

23. The process of claim 1 wherein said first hydrocarbon product stream comprises between about 0.5 wt % and about 12 wt % of $C_{17}$ to $C_{20}$ hydrocarbons.

24. The process of claim 1 wherein said first hydrocarbon product stream has a final boiling point of less than about 350° F. (177° C.).

25. The process of claim 1 wherein said first hydrocarbon product stream has an initial boiling point of at least about 260° F. (127° C.).

26. The process of claim 1 wherein said first olefinic stream contains no more than about 7 wt % of $C_{10}+$ non-normal olefins.

27. The process of claim 1 wherein said first olefinic stream comprises no more than about 30 wt % $C_9+$ non-normal olefins.

28. The process of claim 1 wherein said first olefinic stream comprises at least about 2 wt % to about 50 wt % $C_4$ hydrocarbons.

29. The process of claim 1 wherein said first olefinic stream comprises no greater than about 20 wt % $C_3-$ hydrocarbons.

30. The process of claim 1 wherein said separating (b) is conducted in one or more steps.

31. The process of claim 1 wherein said splitting (c) is such that at least about 20 wt % of said first olefinic stream is provided as said olefinic recycle stream in contacting (a).

32. The process of claim 1 wherein said olefinic recycle stream comprises at least about 20 wt % of said first olefinic recycle stream, based on the total weight of said olefinic recycle stream.

33. The process of claim 1 wherein said first hydrocarbon product stream is saturated with hydrogen to produce a saturated product.

34. The process of claim 33 wherein said saturated product comprises at least about 80 wt % aliphatic hydrocarbons.

35. The process of claim 1 wherein said splitting (c) is such that said first purge stream comprises from about 5 wt % to about 80 wt % of said first olefinic stream.

36. The process of claim 2 wherein said second purge stream is richer in $C_4-$ molecules than said first purge stream.

37. The process of claim 2 wherein said second purge stream comprises at least about 50 wt % $C_4-$ molecules.

38. The process of claim 2 wherein said second purge stream comprises at least about 50 wt % $C_4-$ saturates.

39. The process of claim 2 wherein said second purge stream comprises no greater than about 30 wt % $C_5+$ molecules.

40. The process of claim 2 wherein said second purge stream is in the vapor phase.

41. The process of claim 2 wherein said second olefinic stream is richer in $C_5-C_8$ molecules than said first purge stream.

42. The process of claim 2 wherein said second olefinic stream comprises at least about 50 wt % $C_5-C_8$ molecules.

43. The process of claim 2 wherein said second olefinic stream comprises from about 10 wt % to about 80 wt % $C_5-C_8$ saturates.

44. The process of claim 2 wherein said second olefinic stream comprises no greater than about 30 wt % $C_4-$ molecules.

45. The process of claim 2 wherein said second olefinic stream comprises no greater than about 7.0 wt % $C_{10}+$ non-normal olefins.

46. The process of claim 2 wherein said second olefinic stream comprises no greater than about 30 wt % $C_9+$ non-normal olefins.

47. The process of claim 2 wherein said second olefinic recycle stream comprises at least about 50 wt % of said second olefinic stream.

48. The process of claim 2 wherein said separating (d) of said first purge stream occurs in one or more steps.

* * * * *